US009632035B2

(12) United States Patent
Brukilacchio

(10) Patent No.: US 9,632,035 B2
(45) Date of Patent: Apr. 25, 2017

(54) LIGHT EMITTING DIODE LINEAR LIGHT WITH UNIFORM FAR FIELD

(71) Applicant: Innovations in Optics, Inc., Woburn, MA (US)

(72) Inventor: Thomas John Brukilacchio, Reading, MA (US)

(73) Assignee: Innovations IN Optics, Inc., Woburn, MA (US)

( * ) Notice: Subject to any disclaimer, the term of this patent is extended or adjusted under 35 U.S.C. 154(b) by 277 days.

(21) Appl. No.: 14/307,602

(22) Filed: Jun. 18, 2014

(65) Prior Publication Data

US 2015/0003061 A1    Jan. 1, 2015

Related U.S. Application Data

(60) Provisional application No. 61/840,580, filed on Jun. 28, 2013.

(51) Int. Cl.
*F21V 13/02*    (2006.01)
*G01N 21/88*    (2006.01)
(Continued)

(52) U.S. Cl.
CPC ..... *G01N 21/8806* (2013.01); *G02B 19/0028* (2013.01); *G02B 19/0066* (2013.01); *G02B 27/0927* (2013.01); *G02B 27/0961* (2013.01)

(58) Field of Classification Search
CPC ............ G02B 19/0028; G02B 19/0057; G02B 19/0014; G02B 19/0066; G02B 19/0047; G02B 27/0961; G02B 27/0966; G02B 27/09; G02B 27/0994; G02B 27/0927; G02B 27/0955; G01N 21/8806
(Continued)

(56) References Cited

U.S. PATENT DOCUMENTS 5,900,981 A * 5/1999 Oren ........................ B41J 2/451
                                                       348/E5.139
6,044,096 A * 3/2000 Wolak ...................... G02B 27/09
                                                       372/109
(Continued)

OTHER PUBLICATIONS

International Preliminary Report on Patentability in international patent application No. PCT/US14/42854, mailed on Jan. 7, 2016; 9 pages.
(Continued)

*Primary Examiner* — Anh Mai
*Assistant Examiner* — Arman B Fallahkhair
(74) *Attorney, Agent, or Firm* — Schmeiser, Olsen & Watts LLP

(57) ABSTRACT

Described is a light emitting diode (LED) linear illumination system that includes a linear array of LED groups, high efficiency non-imaging optics and aberration corrected imaging optics. Each LED group can include one or more LEDs. The system provides uniform high intensity in near and far fields. System applications include machine vision and inspection of high reflectivity targets. Illumination can include one or more colors, including white light. The described system has improved thermal and optical performance and is generally more compact and lower in cost relative to conventional systems based on pre-packaged commercially available LED devices.

13 Claims, 21 Drawing Sheets

(51) Int. Cl.
*G02B 19/00* (2006.01)
*G02B 27/09* (2006.01)

(58) Field of Classification Search
USPC ............... 362/268, 244, 555, 235, 227, 237,
362/217.02, 217.03; 359/385
See application file for complete search history.

(56) References Cited

U.S. PATENT DOCUMENTS

| | | | |
|---|---|---|---|
| 6,318,863 B1 | 11/2001 | Taio et al. | |
| 6,371,374 B1 | 4/2002 | Schwartz et al. | |
| 6,433,934 B1* | 8/2002 | Reznichenko | B41J 2/451 |
| | | | 359/621 |
| 6,578,767 B1 | 6/2003 | Barkan et al. | |
| 6,700,709 B1* | 3/2004 | Fermann | G02B 27/09 |
| | | | 359/641 |
| 7,246,923 B2* | 7/2007 | Conner | G02B 27/0994 |
| | | | 362/268 |
| 8,152,347 B2* | 4/2012 | Brukilacchio | G02B 5/021 |
| | | | 362/552 |
| 8,342,725 B2 | 1/2013 | Stein et al. | |
| 8,456,107 B2* | 6/2013 | Salm | F21V 7/00 |
| | | | 315/185 R |
| 8,746,943 B2 | 6/2014 | Brukilacchio | |
| 2006/0039160 A1* | 2/2006 | Cassarly | A47F 11/10 |
| | | | 362/551 |
| 2010/0110660 A1* | 5/2010 | Brukilacchio | B60Q 1/2611 |
| | | | 362/84 |
| 2012/0099308 A1* | 4/2012 | Brukilacchio | G01N 21/8806 |
| | | | 362/235 |

OTHER PUBLICATIONS

International Search Report & Written Opinion in counterpart international patent application No. PCT/US14/42854, mailed on Oct. 17, 2014; 10 pages.

Welford, W.T. and R. Winston, "Fiber Optics Applications", High Collection Nonimaging Optics, Academic Press, Inc., Dec. 28, 1989, pp. 213-215.

\* cited by examiner

LIGHT EMITTING DIODE LINEAR LIGHT WITH UNIFORM FAR FIELD

RELATED APPLICATION

This application claims the benefit of the earlier filing date of U.S. Provisional Patent Application No. 61/840,580, filed Jun. 28, 2013 and titled "Light Emitting Diode Linear Light with Uniform Far Field," the entirety of which is incorporated herein by reference.

FIELD OF THE INVENTION

This invention, in general, relates to providing a continuous or pulsed high intensity line of light suitable for uniformly illuminating the field of view of linear imaging systems used in Bright Field (BF) machine vision applications and more particularly to the use of light emitting diodes (LEDs) in high intensity linear lighting systems. Applications that could make use of such a lighting system include line scan machine vision applications inspecting highly specular surfaces such as Flat Panel Liquid Crystal Display (LCD), solar panel, and semiconductor wafer inspection. In such applications, the camera looks directly into the LED source, as reflected off the sample under test and a source coupling beamsplitter. This requires high uniformity of the radiance at the plane of illumination in order to maximize signal to noise ratio (SNR) and dynamic range of the camera system.

BACKGROUND OF THE INVENTION

High brightness light emitting diode (LED) light sources are in high demand for challenging applications in machine vision. Prior art in the machine vision lighting field typically utilize tungsten or tungsten halogen, metal halide, and xenon arc lamps or more recently, systems incorporating pre-packaged high brightness LEDs. High intensity linear lighting is used to illuminate the field of view of line scan cameras to visualize objects including printed materials on high speed printers and a variety of manufactured products that travel by on a moving conveyor belt or platform for what is typically referred to as web inspection. Objects that have high specular mirror-like reflection, however, require high uniformity of the far field in addition to high near field uniformity. Applications of interest include inspection of liquid crystal displays (LCDs), semiconductor wafers, glass panels, and solar cells. To properly inspect these objects for defects, a beamsplitter is typically used to reflectively couple the light onto the object normal to its surface. The camera typically views the object normal to its surface in transmission through the beamsplitter. Thus, the camera is effectively viewing directly into the line source, which is known as Bright Field (BF) Imaging. Non-uniformity of the far field radiance, from the perspective of the illumination plane, is observed as non-uniformity of the image on the camera. Such non-uniformities reduce signal to noise ratio, that is, camera sensitivity and reduce camera dynamic range. High performance, low cost, compact, and reliable linear lighting with high uniformity both in the near and far field is required for these Bright Field illumination sources.

Until recently, the industry standard was tungsten halogen lamps coupled into typically glass fiber optic bundles arranged in a line and imaged to a line by use of a spherical cylindrical lens. Companies such as Schott Fiber Optics, Dolan Jenner, Volpi, Illumination Technology, and Fiberoptic Technology manufacture such products with a range of available intensities and line lengths. For example, a single twenty four inch long linear lighting system from Schott Fiber Optics is comprised of two separate tungsten halogen light boxes coupled to two one half inch glass fiber optic cables which in turn terminate into a single twenty four inch long length of fiber which images to the illumination plane by use of a cylindrical spherical rod lens. One of the most serious limitations of tungsten halogen technology is that the intensity of the lamps degrades at a fast rate, and for viewing of specular objects, they also are characterized by poor far field uniformity. At full power, tungsten halogen lamps only last between about 50 hours and 500 hours before their initial intensity has degraded by the order of 50% or the lamps fail by filament burn out. The cost of the lamps is not the primary concern, however. It is the cost of shutting down a line to replace the lamp that is primarily driving the need for LED based systems.

Prepackaged LEDs are defined as devices comprising an LED or LED array disposed on top of one or more thermally and electrically conductive materials each with an associated thermal impedance, electrical leads and thermal backplane that are then intended to be attached to yet another board with additional thermal impedance. Examples of prepackaged devices include the Luxeon™ and Rebel™ product lines sold by Philips, the Osram Dragon™ and Ostar™ product lines, and the CREE X-Lamp™ product line.

SUMMARY OF THE INVENTION

Embodiments of a linear lighting system described herein include light emitting diode (LED) light sources with one or more distinct colors including broad band white light. The LED or LED arrays are mounted to a high thermal conductivity circuit board comprising chip on board (COB) technology which can include both the LED and electronic drive components resulting in a more compact and reliable design with improved thermal and optical performance at lower cost relative to pre-packaged based LED systems and other non LED systems such as the industry standard tungsten halogen lamp coupled to optical fibers arranged in a line. In conjunction with high efficiency imaging collection optics and aberration corrected cylindrical optics and light baffles, the resulting LED based line source of the present invention is unmatched in performance by any other commercially available line source lighting system in providing high intensity light with substantially uniform spatial and angular light distributions.

The light from the typically ultraviolet, blue, green, amber, red, infrared or phosphor coated blue (for white light) LED or LED arrays is collected by a linear array of non-imaging concentrators and subsequently imaged to a high intensity line by a hybrid lens incorporating individual lenses per channel to image uniformly to the far field from the region near the output of the collection optic on the LED side and by a common focusing lens on the output side to the illumination plane. The resulting output is characterized by high near and far field intensity and uniformity afforded by the optimized form factors of the optical elements. The length of the line can be readily extended to any arbitrary length as required by a specific viewing application by increasing the number of channels in the long direction of the illuminated line pattern.

In one aspect, the invention features a LED linear illumination system. The system includes a linear array of LED groups. Each one of the LED groups includes at least one LED and has an optical axis that is normal to a surface of each of the LEDs. The system further includes a linear array of collection optics, a linear array of field lenses and a plurality of cylindrical lenses. Each of the collection optics is disposed along a respective one of the optical axes and has an input aperture to collect radiation emitted from a respective one of the LED groups and an output aperture through which the collected radiation propagates. Each cylindrical field lens is disposed on one of the optical axes adjacent to the output aperture of a respective one of the collection optics. Each cylindrical lens has a focal length in a first plane and is disposed on one of the optical axes at a distance from the output aperture of a respective one of the collection optics by substantially a focal length to thereby image light from the output aperture to infinite. The system also includes a cylindrical lens having a focal length in a second plane that is orthogonal to the first plane. The cylindrical lens is disposed at a distance from the input apertures of the linear array of collection optics to form an image of the input apertures in the second plane at an image plane.

In another aspect, the invention features a LED linear illumination system that includes a linear array of LED groups. Each one of the LED groups includes at least one LED and has an optical axis that is normal to a surface of each of the LEDs. The system further includes a linear array of tapers and a linear array of field lenses. Each taper is disposed on a respective one of the optical axes and has an input aperture to collect radiation emitted from a respective one of the LED groups and an output aperture through which the collected radiation propagates. Each cylindrical field lens is disposed on one of the optical axes adjacent to the output aperture of a respective one of the tapers. The system further includes a diffuser disposed adjacent to the linear array of cylindrical field lenses and a plurality of aperture stops each disposed on one of the optical axes substantially adjacent to a surface of the diffuser that is opposite to the linear array of cylindrical field lenses. A plurality of cylindrical lenses each having a focal length in a first plane is disposed on one of the optical axes at a distance from the output aperture of a respective one of the tapers by substantially a focal length to thereby image light from the output aperture to infinite. A cylindrical lens having a focal length in a second plane that is orthogonal to the first plane is disposed substantially at a distance from the input apertures of the linear array of tapers to form an image of the input apertures in the second plane at an image plane. A plurality of baffles each comprising a surface comprising a light absorbing material is arranged parallel to an adjacent pair of optical axes and extends from the linear array of cylindrical field lenses to the plurality of cylindrical lenses.

BRIEF DESCRIPTION OF THE DRAWINGS

The structure, operation, and methodology of the invention, together with other objects and advantages thereof, may best be understood by reading the following detailed description in connection with the drawings in which each part has an assigned numeral or label that identifies the part in the various drawings and wherein.

DETAILED DESCRIPTION

Embodiments of the present invention relate to Light Emitting Diode (LED) lighting arranged such as to produce a line of uniform high intensity light suitable for illuminating the field of view of line scan cameras for use in machine vision applications. In particular, these embodiments of an LED based light source for improved line scan and web inspection systems have a more compact form factor, low cost, higher intensity, and increased lifetime relative to prior art. These embodiments have a highly uniform radiance profile that allows for use in bright field line scan applications that are characterized by substantially specular, or mirror like, reflectance. Thus the embodiments are useful for inspection of objects such as liquid crystal display (LCD) panels, solar cells, high performance window coatings, and semiconductor wafers such as those used to produce large scale integrated circuits. A further advantage is the ability to use multiple colors one at a time or together in any combination and relative intensity to enhance contrast, as different types of defects show maximum contrast for different spectral conditions depending on their wavelength dependent reflectivity. For example, in some embodiments an "LED group" is used in each of the channels. As used herein, an LED group means one or more individual LEDs, or LED die, with each diode emitting light for propagation through optical components arranged along the optical axis of a channel. The system includes a plurality of channels in a linear configuration. In some embodiments, each LED group includes at least a red, a blue and a green LED, and each LED in the LED group can be independently electronically addressed.

Figure 1:
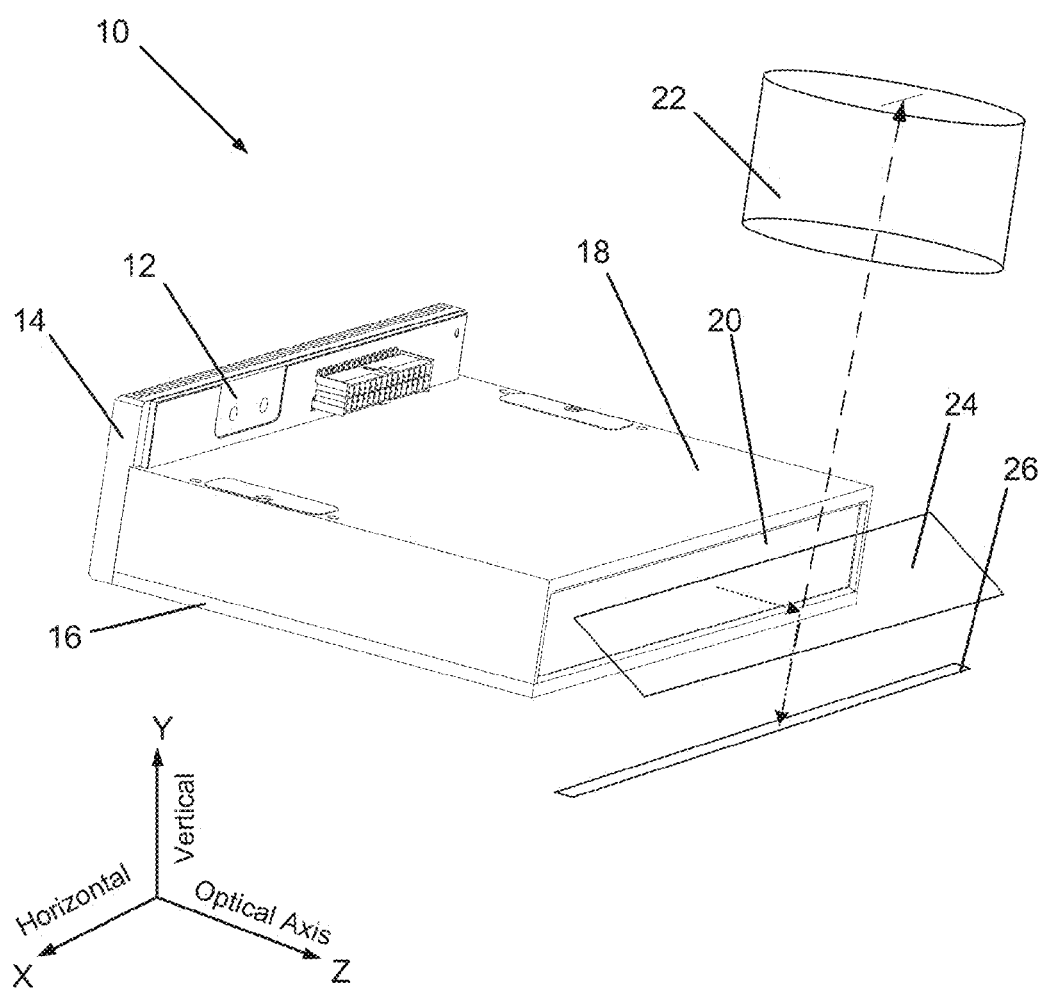
FIG. 1 is a diagrammatic isometric view of a one hundred forty-four millimeter long LED line scan illumination system with high near and far field uniformity. A beamslplitter is shown reflecting the light to the target which is viewed from above through the beamsplitter by a line scan camera.

Referring now to FIG. 1, there is shown a diagrammatic, isometric view of the outside of a preferred embodiment of the LED line source designated generally as system 10. The LED line source system 10 comprises a housing comprised of a top portion 18, a bottom cover 16, an LED board 12, positioned between the housing 18 and a heat sink 14, and an output window 20. External components which are not part of, but are used in conjunction with the line source include a beamsplitter 24 and a line scan camera 22 which images a line 26 produced by the line source as reflected off the beamsplitter 24. The optical axis of the line source is in the positive Z direction and is typically oriented at 45 degrees to the beamsplitter 24. Thus, following the beamsplitter 24, the line source is directed normal to the illumination plane which is coincident with the object being imaged by the line scan camera 22, which has its line of sight in the vertical Y-Axis.

For purposes of describing the line source system 10 acting alone and not in conjunction with the beamsplitter 24 and camera 22, the line will be described in subsequent figures as lying in the X-Y plane and propagating along the optical Z-Axis. The line source system 10, in a manner to be described, yields a high intensity line along the horizontal X-Axis on the order of one hundred and ten (110 mm) millimeters in length and the order of three (3 mm) millimeters wide in the vertical Y-Axis. The nominal focus is approximately eighty four (84 mm) millimeters from the window 20 along the optical Z-axis. The angular extent of the light from the perspective coincident with the line at the plane of illumination 26, looking back in the negative Z direction into the line source, is highly uniform in angular extent along both the X-Z and Y-Z planes with a substantially flat top radiance distribution as will be described. The length of the line can be modified as required for a given application by changing the total number of channels.

Figure 2:
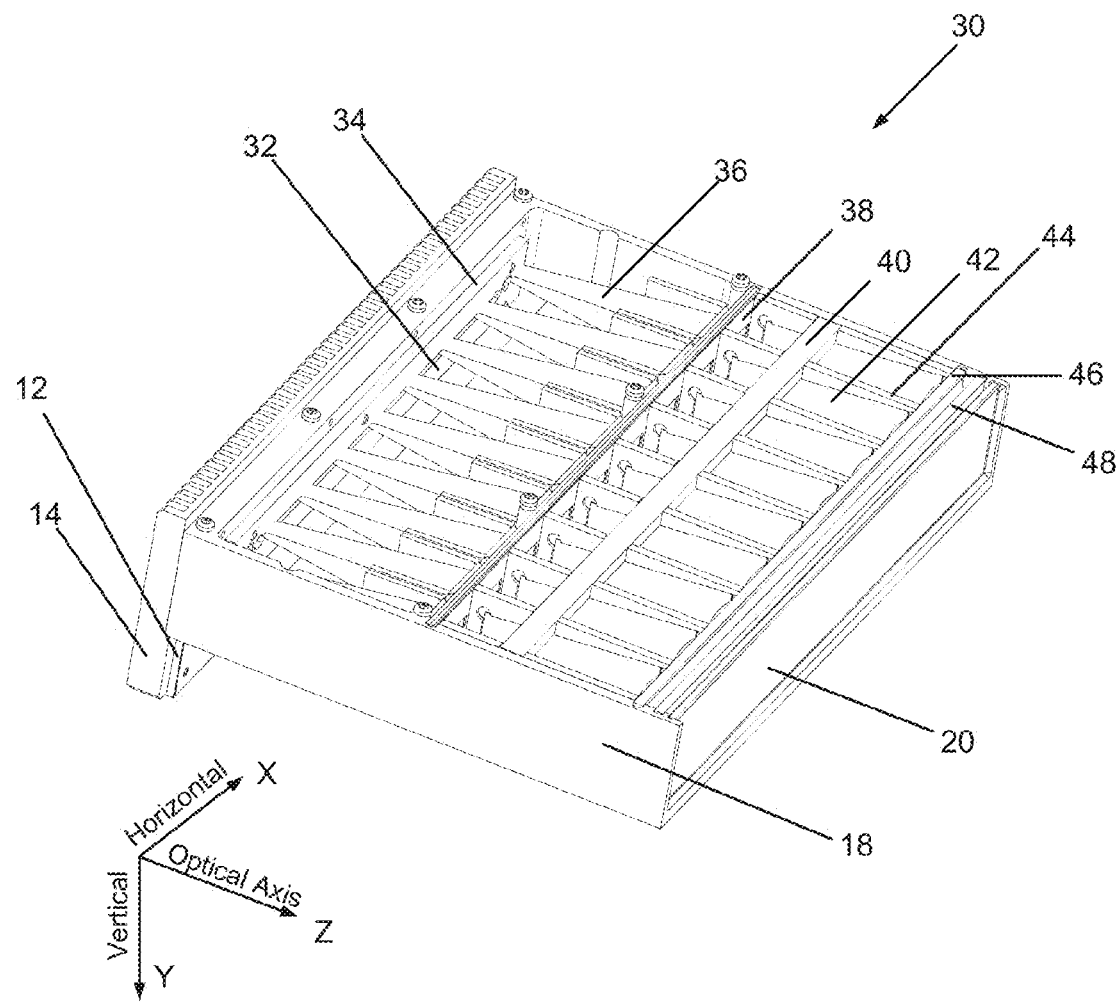
FIG. 2 is a diagrammatic cross-sectional view of the system of FIG. 1 with the line source turned over and the cover removed to show internal components.

Referring now to FIG. 2, there is shown a diagrammatic isometric view 30 of the line source of FIG. 1 positioned upside down with the cover 16 removed to show the internal optical and mechanical components. The non-imaging acrylic optical tapers 36 are positioned to line up to the LED group on the metal core LED board 12 by two aluminum metal bars 32 and 34. The lower bar 32 is positioned via alignment pins to reference to holes in the LED board 12 to assure precise kinematic alignment in the vertical Y-Axis direction relative to the positions of the LED groups. The top bar 34 is then pressed against the taper sides to accurately position their input apertures along the optical axis. A one piece aperture plate 38 is shown near the exit of the nine tapers, one per channel and is comprised of nine apertures to define the limiting angle in the far field in the X-Z plane. Light baffles comprising a holder 44 with a light absorbing material 42 attached to both sides of the baffle holder 44 are aligned to each channel by groves machined into the bottom of the housing and by the alignment bar 40 on the top. They are aligned along the Z-Axis by being positioned tightly between the aperture 38 and the lens 46. The light leaving each taper is made more uniform in the far field, that is in angle space, by a diffuser to be described below which is positioned between the output face of the tapers 36 and the aperture plate 38. The light then passes to the lens 46 which acts on the far field in the X-Z plane by individual lens sections per channel to be described in detail below and then focused to the illumination plane by the front portion of lens 46 after having passed through output window 20.

Figure 3:
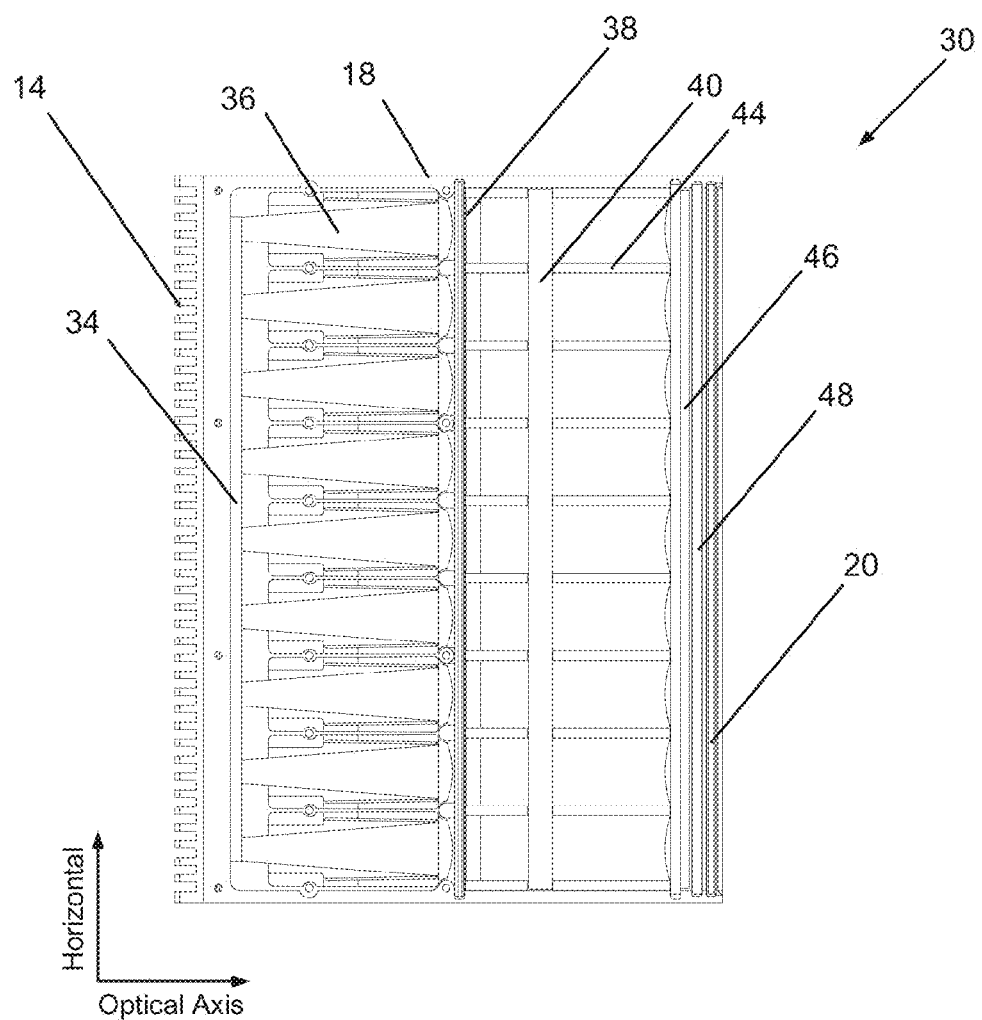
FIG. 3 is a diagrammatic top view of the system of FIG. 2 showing nine individual LED and optical channels that comprise the LED module including a homogenizing taper, diffusers, and a hybrid field and cylindrical focus lens.

Referring now to FIG. 3, there is shown a diagrammatic elevational top view of the system 30 of FIG. 2. The optical element 48 between lens 46 and output window 20 can take the form of a low angle spreading diffuser or an additional focusing lens as required for specific imaging applications. The heat sink 14 has vertical fins which allow the line source to be passively cooled by free convection. The mounting bracket that holds system 30 in place would also dissipate some of the heat as thermal pads are placed between the housing and the brackets for just this purpose. If higher drive currents were required for specific applications, other cooling means could be added such as forced convection by fan, blower, or ducted air, heat pipes, and water cooling systems.

Figure 4:
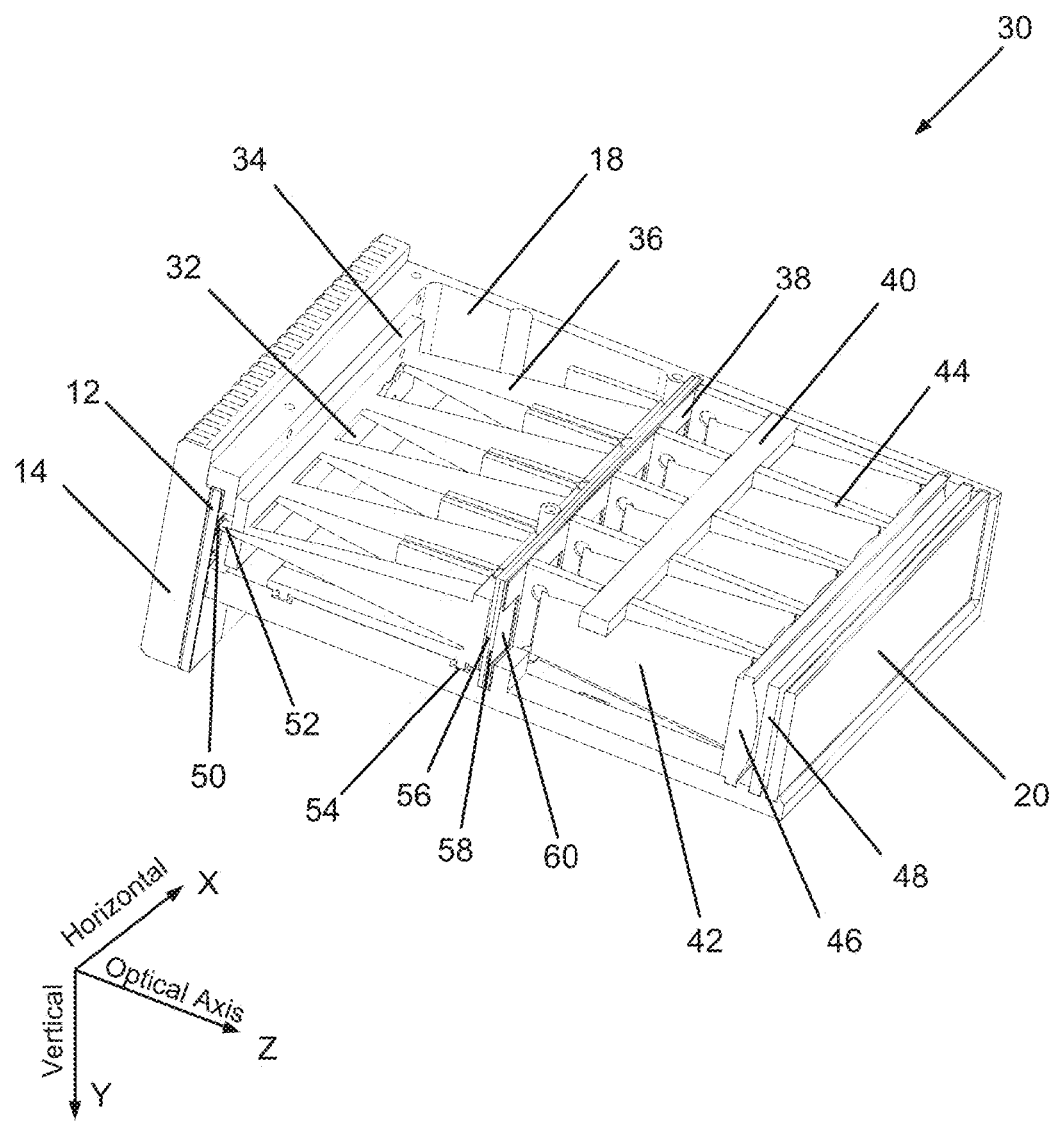
FIG. 4 is a diagrammatic cross-sectional view of the system of FIG. 3 exposing detail of the taper, diffusers, field aperture, light baffle, focusing lens and exit window.

Referring now to FIG. 4, there is shown a diagrammatic cross-sectional view of the system 30 of FIG. 2, revealing the LED group 50 on the LED board 12 which is coupled to the input aperture 52 of taper 36 for the central channel. Also visible in this cross-sectional view is the kinematic feature 54 comprised of a set of pins on the bottom of the molded taper collection optic 36 and a mating set of kinematic slots on the bottom of the housing 18 which act to align the taper 36 to each LED group on the LED metal core board 12. Two diffusers 56 and 58 are shown positioned between the output of the taper 36 and the far field aperture plate 38 with aperture opening 60. The function of the diffusers 56 and 58 is to increase the far field uniformity in the X-Z plane.

Tapers such as 36 comprise a non-imaging optic that collect light at their input side and emit light at their output side which is highly uniform in the near field, that is, substantially near the output face of the taper, are characterized by relatively poor far field uniformity, that is, intensity pattern at a distance large compared to the output face dimensions of the taper, unless the taper is extremely long. In the case of the system 30 of FIG. 4, the length of the taper that can be used to produce high uniformity with multiple LED sources of different spectral characteristics at its input would be unreasonably long. This would render the optic too expensive if it could be made at all and the line source too long and costly for general application. The far field that results from a taper is dependent on the position of the sources relative to the taper's input aperture dimensions. In the case of system 30, the vertical extent of the input aperture is fully filled by the LED group, and in fact is overfilled to account for finite alignment tolerances. Since the vertical axis is fully filled, the far field emitted in the Y-Z plane is highly uniform. The horizontal dimension of the taper is not fully filled by each color, as there are multiple LEDs in that direction to allow for multiple colors. Thus, the far field in the X-Z plane is not uniform and can be understood by considering a kaleidoscope which results in multiple mirror reflections of the source, in this case different discrete LEDs characterized by different spectral colors.

Although it is possible to switch the orientation of the LED group and make the wide dimension of the taper 36 input aperture in the vertical Y-Axis direction, that would result in a wide line width in the illumination plane, which is not useful since the field of view of the line scan camera is narrow in the narrow dimension of the line, even when a time delay and integration (TDI) charged coupled device (CCD) is employed, and would therefore result in unwanted stray light.

Thus, it is desired to improve the far field in the X-Z plane at the output of the tapers by use of a substantially planar homogenizing element which acts substantially on spreading light in the X-Z plane only. The reason it is not good to spread light in the Y-Z plane is that it would result in an increase in the line width at the illumination plane, which would result in a decrease in the intensity and radiance. Preferred embodiments of the diffusers include elliptical and line holographic diffusers of the kind manufactured by companies such as Luminit of Torrance, Calif., or "Engineered Diffusers" by companies such as RPC of Rochester, N.Y. A preferred embodiment contains a single diffuser with a full width half maximum (FWHM) angular Gaussian beam spread of 40 degrees by 0.20 degrees. It is preferred not to have any spreading in the Y-Axis, however, this is generally difficult to achieve in practice with such diffusers. Such substantially one-dimensional diffusers may contain surfaces comprising selectively textured versus non-textured areas, holographic elements, and macroscopic refracting elements. A preferred embodiment of diffusing elements includes lenticular arrays, such as those manufactured by Reflexite Energy Solutions, of Rochester, N.Y. The advantage of an ideal lenticular, which is comprised of a long array of parallel cylindrical lens sections all attached to a glass or plastic substrate, is that they act to spread light in only one axis, thereby minimizing line width and maximizing near field intensity and radiance at the illumination plane. The curved surface of the lenticular would be in the X-Z plane and extruded along the Vertical Y-Axis direction. A preferred embodiment would use only one of the two diffusers shown in FIG. 4. More than one diffuser is shown to indicate that multiple diffusers 56 and 58 could be stacked to increase the degree of diffusing, but there is then some loss in light due to Fresnel reflections, that is, losses at air to glass interfaces, or air to plastic interfaces, unless costly anti-reflection coatings are added.

The baffles comprising the holders 44 and covered on each side with a light absorbing material 42 are there for the purpose of substantially extinguishing stray light emitted in the X-Z plane resulting from the spreading of light coming out of the diffusers. It is necessary to use a sufficiently large diffusing angle as to assure that light that reaches the individual lenses on the back side of lens 46 has a uniform intensity over the required far field angular extent. Thus, some light will necessarily extend beyond the acceptance angle of the lens segments in the X-Z plane and must be extinguished. If the baffles were removed, the light from each channel would spill over into the adjacent channels and then be refracted into large far field angles by the adjacent channel's far field lens on the LED side of lens 46. If such light did not reach the camera directly, it could result in scattering and thus background noise that would reduce contrast on the camera. The absorbing material in a preferred embodiment is a nanoformed black coating applied to metal foil or metal parts, such as manufactured by Acktar, of Kiryat-Gat, Israel, or flock paper, which is a black velvet material sold by Edmund Optics, of Barrington, N.J. Other choices for black absorbers include Engine Black paint, bead blasted and black anodized aluminum, and textured black polymers. Shiny black surfaces perform poorly due to their highly specular Fresnel component at grazing incidence and should be avoided.

The element 48 of FIG. 4 can be an auxiliary optical element that can serve a number of functions including additional homogenizing of the far field to further improve uniformity and as a modification to the X-Axis focal point, if something other than focusing to infinite in the X-Axis is desired. The far field in the X-Z plane is an image of the aperture 60 achieved by placing the lens on the LED side of hybrid lens 46 substantially at a focal distance away from aperture 60. This configuration results in a substantially flat radiance profile along the X-Axis, however, it also results in imaging structure of the diffusers into the far field. That is to say, if the diffusing features on the diffuser are not sufficiently small, then there will be some modulation in the X-Axis far field due to imaging the structures. In such a case, a small degree of diffusing at the position of element 48, which for the X-Axis far field imaging is at its aperture stop, results in a smoothing of the high frequency structure, if present. This is also motivation for using finely pitched diffusers 56 and/or 58.

The degree of diffusing that is required for a given application is dependent on the number of individual colors LEDs in the LED group and their relative position at the input aperture 52 of the taper 36. For example, if only a single color LED is used and substantially fills the entire input aperture, then the far field is sufficiently uniform as to require no diffusers in the positions 56 and 58. This would also maximize the near and far field intensity, since light would not be lost at the baffles. It would still be necessary to overfill the far field lenses on the LED side of lens 46 in order to assure far field uniformity between the individual channels, that is, from the perspective of looking back into the line source from a position midway between the centerline of two adjacent channels. Otherwise there would be an intensity dip looking directly into the region along the Z-Axis and in the plane between two adjacent channels. This is also why it is important to make sure the radius between two adjacent far field lenses on the back side of lens 46 is minimized. Alternative embodiments of LED groups could use a mosaic of smaller LEDs to better distribute the different color sources and thereby decrease the burden on the diffuser. A disadvantage of using smaller LEDs is that alignment tolerances are tighter and thus more difficult to achieve and smaller LED in general have lower output since proportionally more of the LED surface is obscured by the electrodes.

Figure 5:
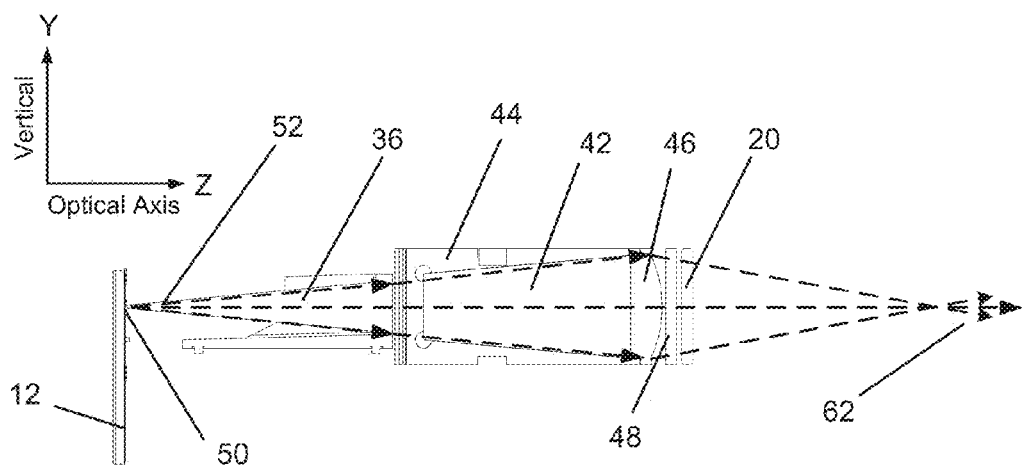
FIGS. 5A and 5B show diagrammatic views of the system of FIG. 1 with the the housing and heat sink removed in the plane orthogonal to the length of the line and in a plane containing the length of the line, respectively. Optical rays are indicated by the arrows to depict ray paths traversing from LEDs to the illumination plane along the positive Z-axis.
Figure 5:
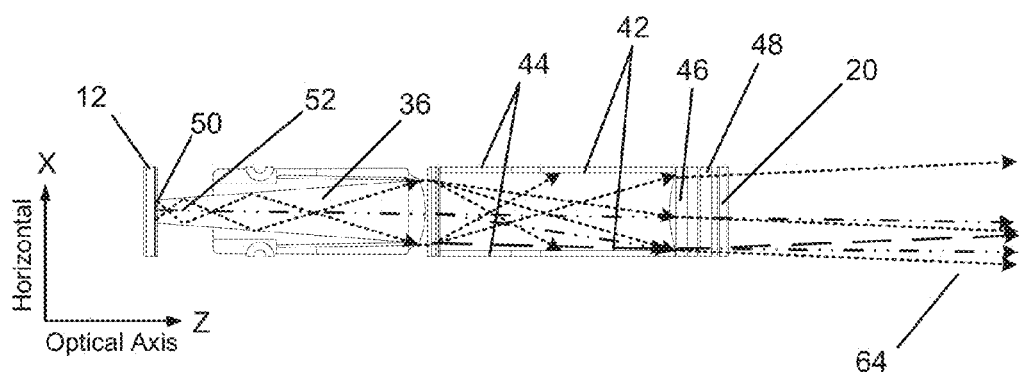

Referring now to FIG. 5A, there is shown a diagrammatic cross-sectional view of the system 30 of FIG. 4 with the housing removed showing only the LED board and the optical elements with rays 62 drawn in to indicate ray paths. The rays extend from the LED group 50 on the LED metal core board 12 into the collection input aperture 52 of the taper 36. Since there is minimal diffusing in this Y-Z plane the taper and diffusers act substantially as windows. The angle of the rays with respect to the optical Z-Axis increases slightly due to refraction as they leave the taper for off-axis rays and are directed toward the lens 46 which has power on the side opposite the LED array which acts to focus the rays 62 to the line focus coincident with the image plane of the line scan camera. Thus, in order to achieve uniform radiance at the illumination plane in the Y-Axis, it is desirable that the lens 46 be filled uniformly along the vertical Y-Axis direction. This results from fully filling or overfilling the input aperture 53 of the taper 36 along the Y-Axis. Since the LEDs of different colors are distributed along the X-Axis, they all are uniformly filled in the Y-Axis and thus all colors yield high uniformity of the radiance in the Y-Axis.

Referring now to FIG. 5B, there is shown diagrammatically, a top view of a single channel of the system 30 of FIG. 4, showing the homogenizing effect of the taper 36 with multiple reflections of the rays 64 as they traverse the taper 36 from the LED group 50 to the output of the taper 36. The output of the taper 36 is terminated in a cylindrical lens which acts as a field lens by redirecting rays that would otherwise be lost at the baffle 42 and directs their chief ray toward the center of the far field lens on the LED side of lens 46. This acts to improve overall efficiency and therefore the near and far field intensity at the illumination plane. It is instructive to follow the path of a single ray traversing down the taper 36. As the limiting ray entering the input aperture 52 of taper 50 enters the optical material, its angle with respect to the optical axis is decreased in accordance with Snell's Law of optical refraction since the optimal medium between the LED group and the taper input aperture is air. The use of no index matching medium maximizes brightness due to the fact that most state-of-the-art LEDs have incorporated into their structure features which act to increase the amount of light entering the air from the LED semiconductor junction so that the advantage of index matching is less than no index matching with respect to system brightness. Additionally, if it were index matched the angle of the light incident on the side walls of the taper would be such that total internal reflection would not be supported and the rays would exit out the walls of the taper. The illustrated embodiment does not use index matching medium and does make use of the high efficiency resulting from the total internal reflection of the rays as they traverse down the non-imaging tapered collection optic. With reference to the ray that is shown at the top side of the output field lens of the taper of FIG. 5B, the ray is deflected over a range of angles by the diffusers at a macroscopic level which is indicated by the three rays leaving this point, the top ray entering the center of the far field lens on the LED side of lens 46, the middle ray entering the bottom of the lens 46 and exiting as the limiting angular ray in the far field shown exiting the window at the bottom, and the lower most ray which is directed toward and absorbed by the lower baffle 42. It should be apparent to those skilled in the art that the far field radiance distribution at the illumination plane is a result of the imaging of the aperture 60 of FIG. 4 by lens element 46 into the far field resulting from placing the lens 46 at substantially a focal distance from aperture 60 and that further, the angular extent of the far field in the X-Axis is limited by and determined by the physical width of the aperture 60 along the X-Axis direction. It should further be evident that any defects or large features in the plane of the aperture 60 are imaged to infinite, that is, to the far field in the X-Axis necessitating the use of diffusers with small features relative to the width of the aperture along the X-Axis. The precise dimensional constraints would be dictated by the far field high frequency requirements. Typical holographic diffusers such as those manufactured by Luminit and small pitch lenticulars on the order of a 0.20 mm pitch or smaller result in sufficiently uniform far fields. Again, if desired, a low angle diffuser can be positioned at optical element 48, which is the stop of the far field lens 46 in this plane, and as such is not imaged, but would smear out high frequency structure in the plane of aperture 60 of FIG. 4.

Figure 6:
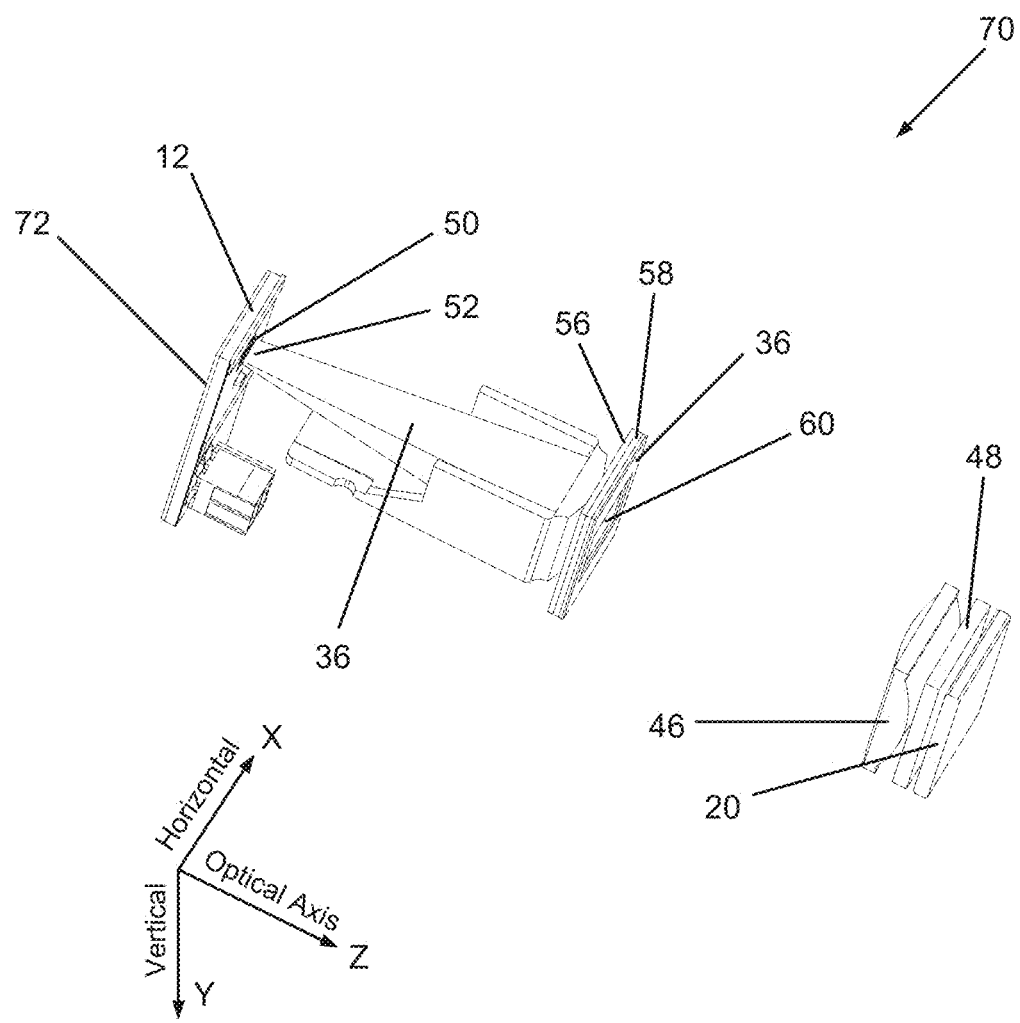
FIG. 6 is a diagrammatic isometric view of a single channel of the system of FIG. 2.

Referring now to FIG. 6, there is shown a diagrammatic isometric view 70 of a single channel of the system 30 of FIG. 2. A thermal pad 72 is shown on the back side of the metal core LED board 12 which is compressed between the heat sink 14 of FIG. 1 and the LED board 12 to allow for thermal conduction to the heat sink. A preferred embodiment uses a thermal SIL900 thermal pad manufactured by The Berguist Company, which also manufactures the metal core LED board 12. The two orthogonal cylindrical lens components of lens 46 are clearly visible, as well as the far field aperture stop 60 at the exit of the diffusers 56 and 58. This optical channel can be repeated along the X-direction for any arbitrary length, depending on viewing requirements imposed by the camera field of view and object being inspected. The current to each LED can be adjusted to maximize the uniformity of the line intensity profile along the X-Axis to account for differences in the outputs from the individual LEDs and to account for alignment tolerance and finite differences in optical elements.

Figure 7:
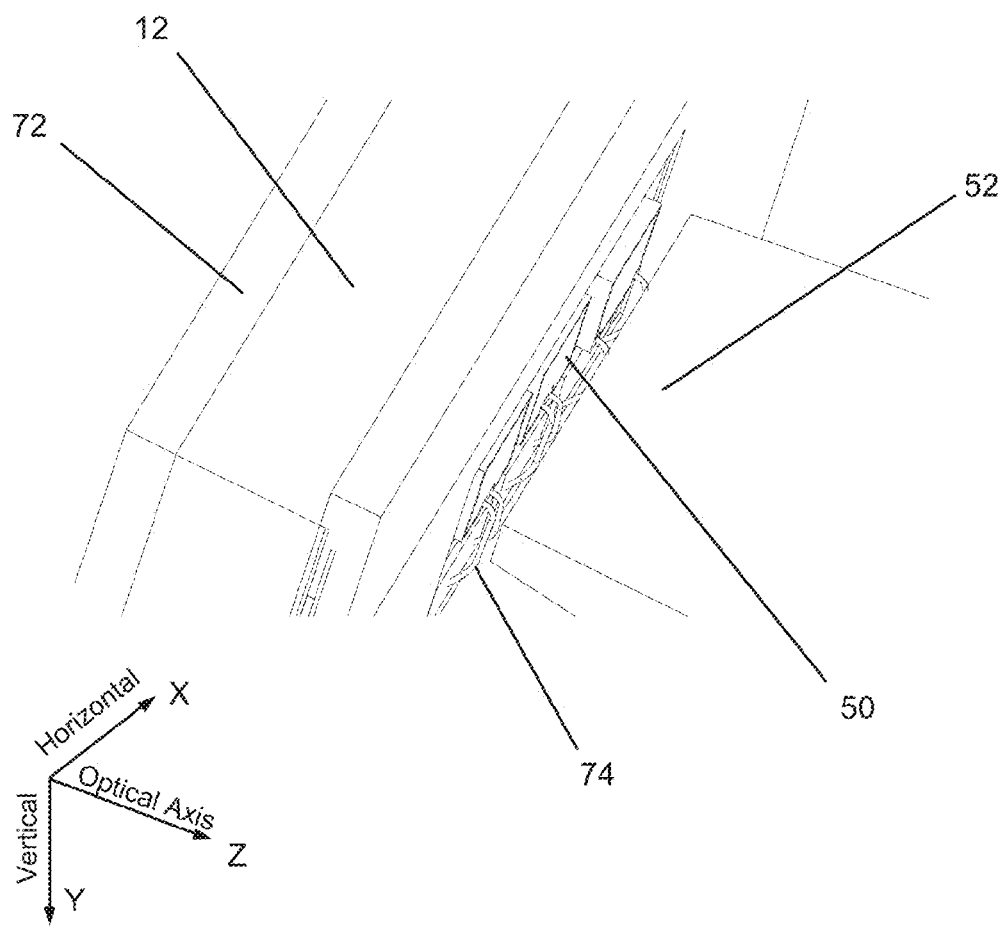
FIG. 7 is a diagrammatic isometric close up view of FIG. 6 indicating detail of the LED attached to the metal core board and the input to the tapered collection optic.

Referring now to FIG. 7, there is shown a close up of system 70 of FIG. 6, showing detail of the region on the board comprising the LED group 50, wire bonds 74, and input aperture 52 of the taper 36. In a preferred embodiment, the LEDs are attached by means of solder paste reflow. The wire bonds can be either wedge or ball bonds and use gold or aluminum wire of sufficient size to pass the current required for the highest required intensities for a given application. Typically either 1.5 mil or 2.0 mil gold wire is used. The taper input apertures 52 are spaced a distance on the order of 100 microns to 300 microns from the LED group 50, close enough to achieve high coupling efficiency, but sufficiently far as not to damage the LEDs, wire bonds, or input aperture of the taper.

Figure 8:
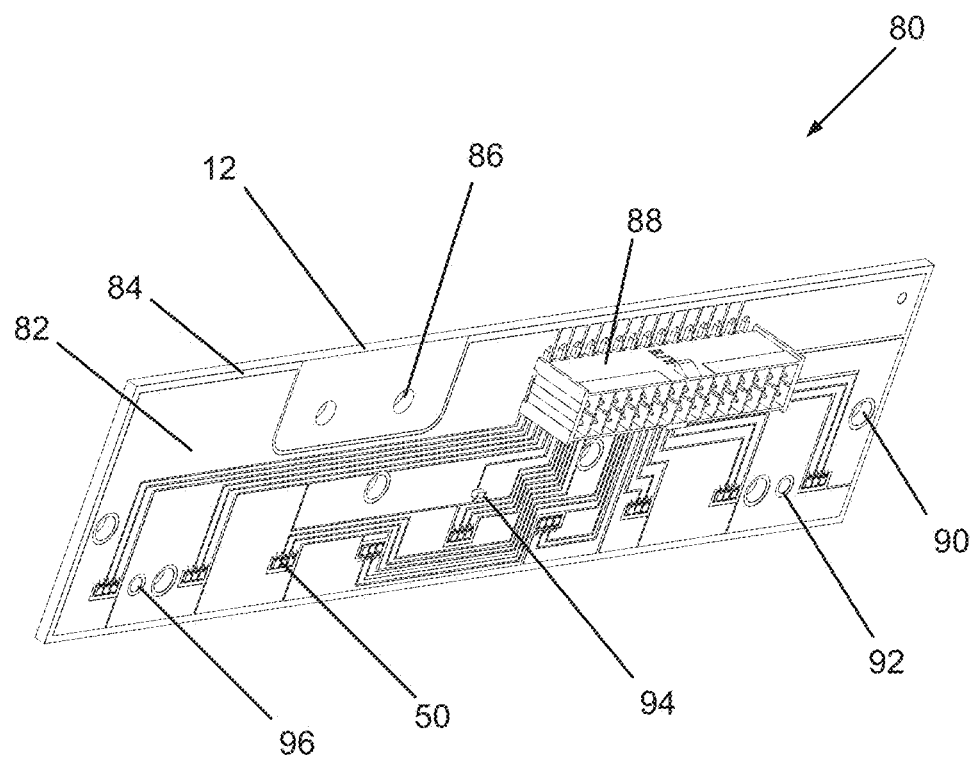
FIG. 8 is a diagrammatic isometric view of the metal core LED board of the system of FIG. 1.

Referring now to FIG. 8, there is shown a diagrammatic isometric view 80 of the LED "Chip-on-Board" (COB) metal core PCB comprised of metal core 12, dielectric layer 84, foil layer 82 to which the wire bonds are routed, a surface-mount thirty (30) pin connector 88, LED groups 50, one each per nine independent channels, a temperature sensing thermistor 94, four each mounting holes 90, and kinematic mounting holes 92 and 96. The board is most optimally made out of copper, having a high thermal conductivity on the order of 400 W/m-K which provides excellent thermal conduction and heat spreading and is manufactured to design specifications by The Berguist Company, of Chanhassen, Minn. Alternative board materials include aluminum, aluminum nitride, beryllium oxide, silicon, silicon carbide, graphite and polycrystalline CVD diamond as well as planar heat pipes, also referred to as vapor chambers. If desired, a light sensor such as a photodiode can be added to the board to monitor or close the loop on optical intensity as it varied with time and temperature. The kinematic holes 92 and 96 line up with a hole and slot in the housing to allow for precise and repeatable positioning of the LED board relative to the housing. The LED groups, which can be comprised of any color LEDs available, are attached directly to the gold coated copper core to maximize thermal performance, intensity and temperature dependent lifetime. The two holes 86 allow for the attachment of the common anode. In a preferred embodiment, the cathodes from each of three color LEDs for each of nine channels are independently addressed by connection to a unique pin on electrical connector 88. An electrically insulating solder mask (not shown) is typically placed over the foil layer. The solder mask also acts to minimize cost by minimizing the metal that gets gold coated as well as to prevent solder from shorting out between traces, typically on the order of 25 microns thick. The thickness of the board is selected to offer the best tradeoff between heat spreading, minimizing thermal impedance, minimizing trace gap width, and minimizing weight and cost and is on the order of 2 millimeters thick for a preferred embodiment. The LEDs are attached directly to the gold coated copper to minimize thermal impedance which in turn maximizes light output at a given current and maximizes temperature dependent lifetime. If serial connection of the LEDs is required, the LEDs can be attached to the top of the foil layer at the expense of thermal performance and lifetime, but sometimes this is a desirable tradeoff due to electrical drive requirements.

Figure 9:
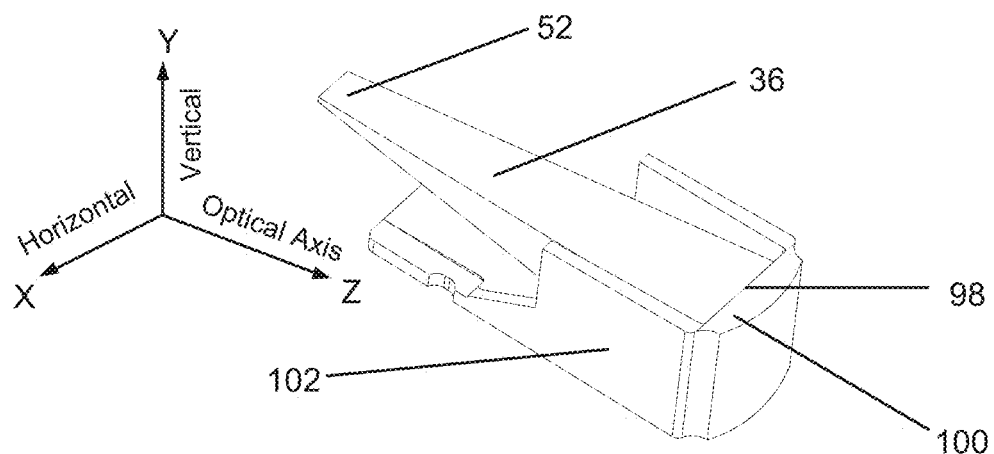
FIG. 9A through 9C show three different diagrammatic isometric, top and side views, respectively, of the tapered collection optic of FIG. 2.
Figure 9:
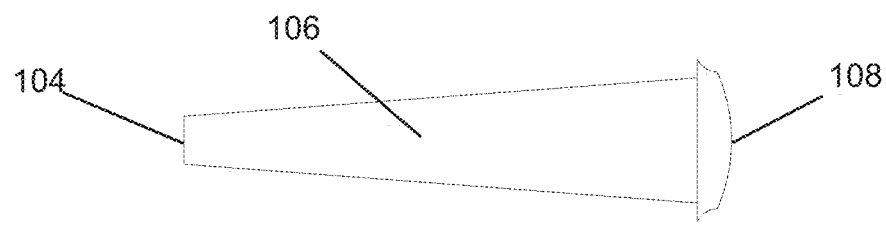
Figure 9:
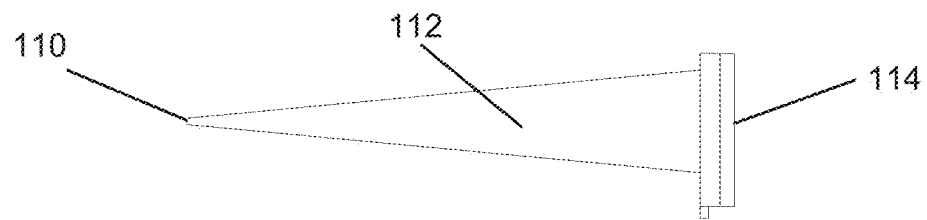

Reference is now made to FIG. 9A which shows a diagrammatic isometric view of the non-imaging tapered collection optic 36 with input aperture 52, output aperture 98, integral cylindrical field lens 100 and support frame 102. The frame allows the optic to be positioned accurately. The semicircular holes in the bottom of the frame allow the frame to be secured by screws on both sides to hold the frame toward the bottom of the housing 18 of FIG. 2. The holes are positioned relatively close to the input aperture along the Z-Axis in order to minimize the movement of the position of the input aperture relative to the LED group 50 of FIG. 4 to account for the finite differential thermal expansion between the aluminum housing and the plastic. A preferred embodiment is made out of a UV920 grade PMMA (acrylic) which is characterized by minimal yellowing due to exposure to short wavelength light. Other materials that can be used include other optical grade acrylics, polycarbonates, cyclic olefins, silicones, glasses, and optical crystalline materials. In the case of ultraviolet (UV) LEDs, glass such as BK7 can be used as such glass does not yellow from exposure to ionizing photons. In that case, the diffusers can also be made out of a glass, or potentially glass and silicone hybrid material to increase resistance to yellowing. Likewise the other optical elements can be made out of similar non-yellowing materials to maintain performance of the product life if short wavelength ionizing LEDs are used. In a preferred embodiment, the dimension of the input aperture along X is 4.20 millimeters and along Y, 0.55 millimeters, a taper length of 45 millimeters along the Z-Axis, a Y-Axis output dimension of 9.0 millimeters, and an X-Axis output dimension of 11.0 millimeters.

FIG. 9B shows a top view of the taper 36 of FIG. 9A indicating a long dimension 104 of the input aperture in the X-Z plane, a top surface 106, which is symmetrically identical to its bottom surface, and a curved lens surface 108, comprising the lens that redirects the extreme rays in the X-Z plane toward the center of the lens 46, with respect to the local central optical axis of each taper. Likewise, FIG. 9C shows a side on view of the taper 36 of FIG. 9A indicating a narrow dimension 110 of the input aperture in the Y-Z plane, a side surface 112, which is symmetrically identical to the far side surface, and a straight output face 114 of the lens 100 indicating the taper's integral field lens has power in only one plane. The frame has been substantially hidden in FIGS. 9B and 9C to show the detail of the taper side walls. The dielectric solid taper is one of many forms that can be used in this application. Other nonimaging collection optics that can be used include compound parabolic concentrators of the type described by Winston and Welford in a book entitled "High Collection Nonimaging Optics" published by Academic Press and are made of tilted and shifted parabolic sections according to the edge ray principle. The CPCs are truncated near the entrance according to the theta by theta concentrators described for the case of rotational symmetry by Welford. To make sure that the exit surfaces end at the same distance from the entrance aperture, the shorter CPC is extended by a straight wall up to the output face. The advantage of the CPC over a straight taper is that CPCs are characterized by improved concentration ratios for a given output numerical aperture (sine of exiting half angle also designated as NA). The disadvantage, however, is that the output intensity distribution and far field is more sensitive to the position of the sources at the entrance aperture. Thus, if the entrance aperture is fully filled with a single color LED, the CPC would result in the highest efficiency and shorter length relative to a taper. If however, the CPC was not fully filled, the intensity would have compromised uniformity. One can, however, include a straight homogenizing section to the input aperture of the collection optic to reduce the sensitivity and thereby get the best of both, high intensity and reduced sensitivity to input aperture uniformity. In some cases, tooling costs are considered, as in general it is easier to make tooling for straight walled tapers rather than curved CPCs. Another option is to use the CPC in only the vertical plane with no CPC section in the horizontal plane, which would not require a homogenizing light pipe at the input aperture and can decrease tooling costs over using CPCs on all sides. Other embodiments of a collection optic include stepped tapers, that is, taper sections at different angles with respect to the optical axis. Additionally, hollow mirrored versions of all these optics are feasible, but may be costly to produce and require very high performance mirrored coatings due to the multiple bounces in the X-Z plane. Anti-reflection coatings can be added to the output faces to increase throughput at the expense of added cost. The curvature of the cylindrical lens 100 of FIG. 9A can be spherical or aspherical, depending on the specific far field requirements.

Figure 10:
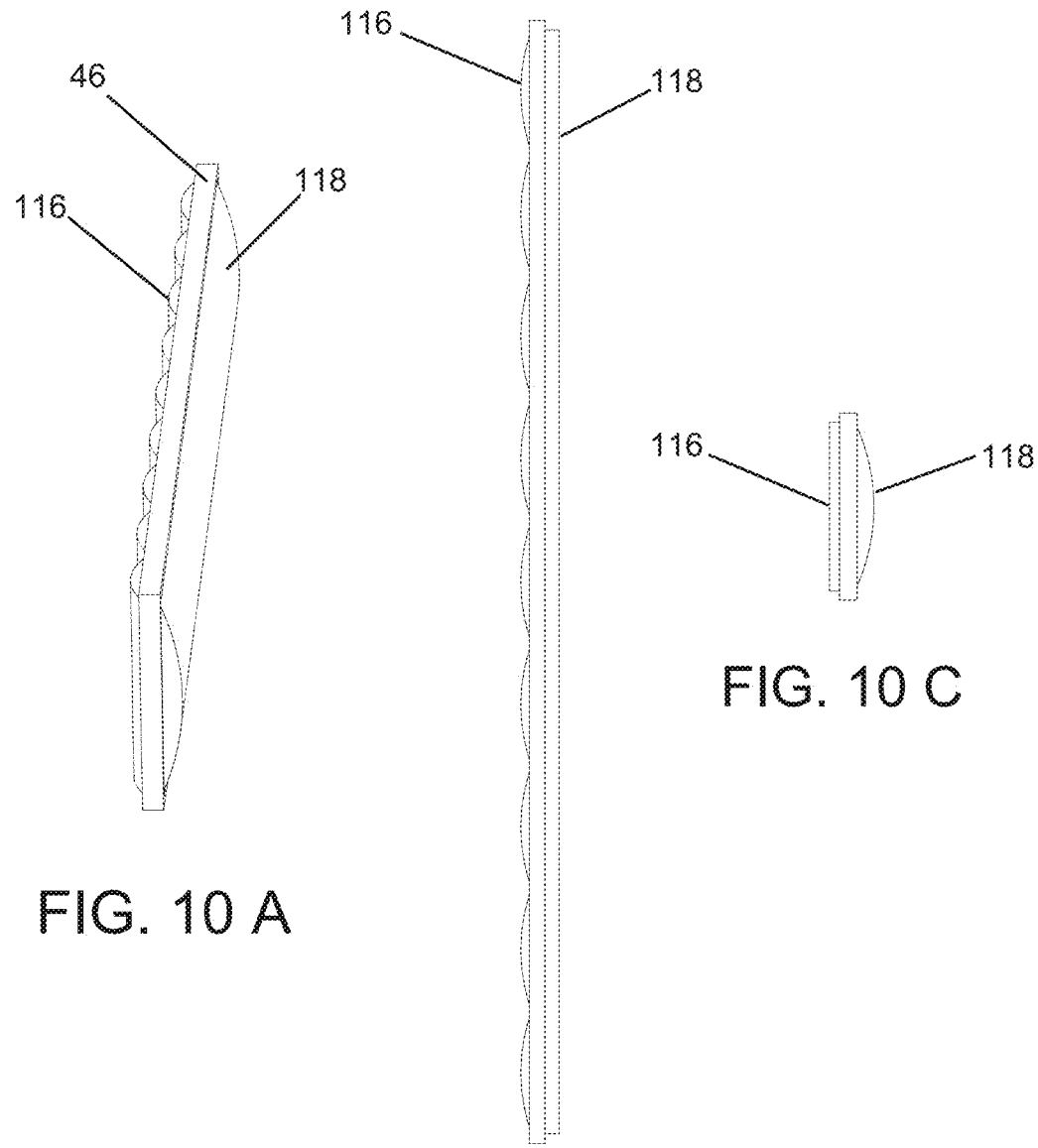
FIG. 10A through 10C show three different diagrammatic isometric, top and side views, respectively, of the combined lens incorporating far field lenslets on the left and common line focus lens on the right of the focus lens of FIG. 2.

Referring now to FIG. 10A, there is shown a diagrammatic isometric view of the lens 46 of system 30 of FIG. 4. The lens is comprised of nine individual cylindrical lenses 116, one per channel, with power only in the X-Z horizontal plane which acts to image the uniform output of the diffuser 58 at aperture 60 of FIG. 4 to the far field in the X-Z plane. In a preferred embodiment, the lens has an aspheric shape, but a spherical shape could be used in some cases. Using a conic constant is useful in trading off various parameters during optimization. The choice of center to center channel spacing is not random, but is optimal for a given specification for focal distance from the exit window 20 to the illumination plane as well as to the far field angular requirement in both axes. The center to center spacing for the system 30 of FIG. 2 was optimal for 16 mm. The far field angle in the X-Z plane is determined by the width of the aperture 60 in FIG. 4 in the X-Z plane, the distance between the aperture 60 and the cylindrical lens 116 on hybrid lens 46 and the channel to channel separation. The nine far field imaging lenses 116 are shown from a diagrammatic top view in FIG. 10B. The edges of the intersection between adjacent lenses actually comes together in a sharp point, which is obscured from view in FIG. 10B due to the wider extent of the frame. As described previously, it is important that the lenses extend up to each other at adjacent edges with minimal radius to prevent a dip in the far field intensity as observed looking back into the line source in the negative Z direction midway between two channels. It is also important that the front edge of the baffle not block those rays extending from the line between two adjacent field lenses 116 as they come from the near extents of the aperture 60. This is a function of how thick the baffle needs to be from a mechanical perspective. Thus, a baffle with a finite thickness would need to be terminated some distance from the seam between two lenses 116 to prevent blocking rays, which if not done would result in a dip in the far field intensity midway between channels. An end-on, side view of lens 46 is shown in FIG. 10C showing the curvature of the front common line-focusing lens section 118, which in a preferred embodiment is aspheric to minimize loss in intensity due to spherical aberration that would otherwise exist for a spherical lens. In a preferred embodiment the lens material is made from a high performance optical grade acrylic UV920, as was the taper. For shorter line source focal length systems preferred embodiments may use polycarbonate, MAKROLON LED2045, manufactured by the Bayer MaterialSience. The advantage of using polycarbonate for short focal lengths is that the increased bending requirement for rays leads to increased curvature of the lens and the higher index of refraction of the polycarbonate on the order of 1.57 relative to that of UV920 acrylic on the order of 1.49, leads to a larger radius of curvature, thereby decreasing spherical aberrations and lens center thickness. One disadvantage of the higher index, however, is increased Fresnel reflective losses, but these losses can be overcome by use of anti-reflection coatings, if desired.

Figure 11:
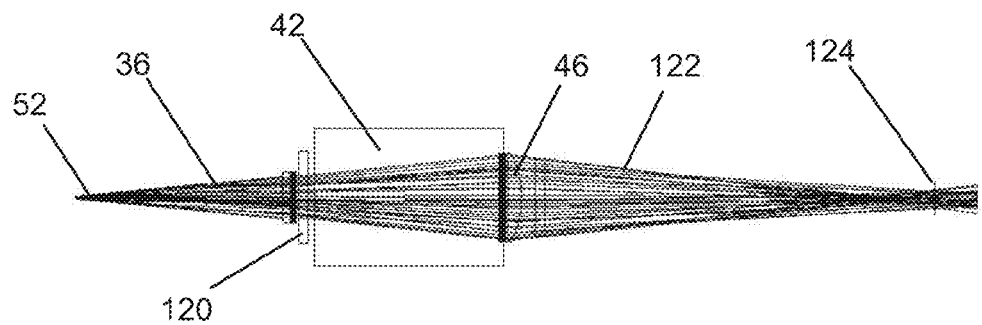
FIGS. 11A and 11B show diagrammatic ray traces from the exit of the taper thourgh the diffuser, field and focus lens and window to the illumination plane for a side on view in the Y-Z plane and top view in the X-Z plane, respectively.
Figure 11:
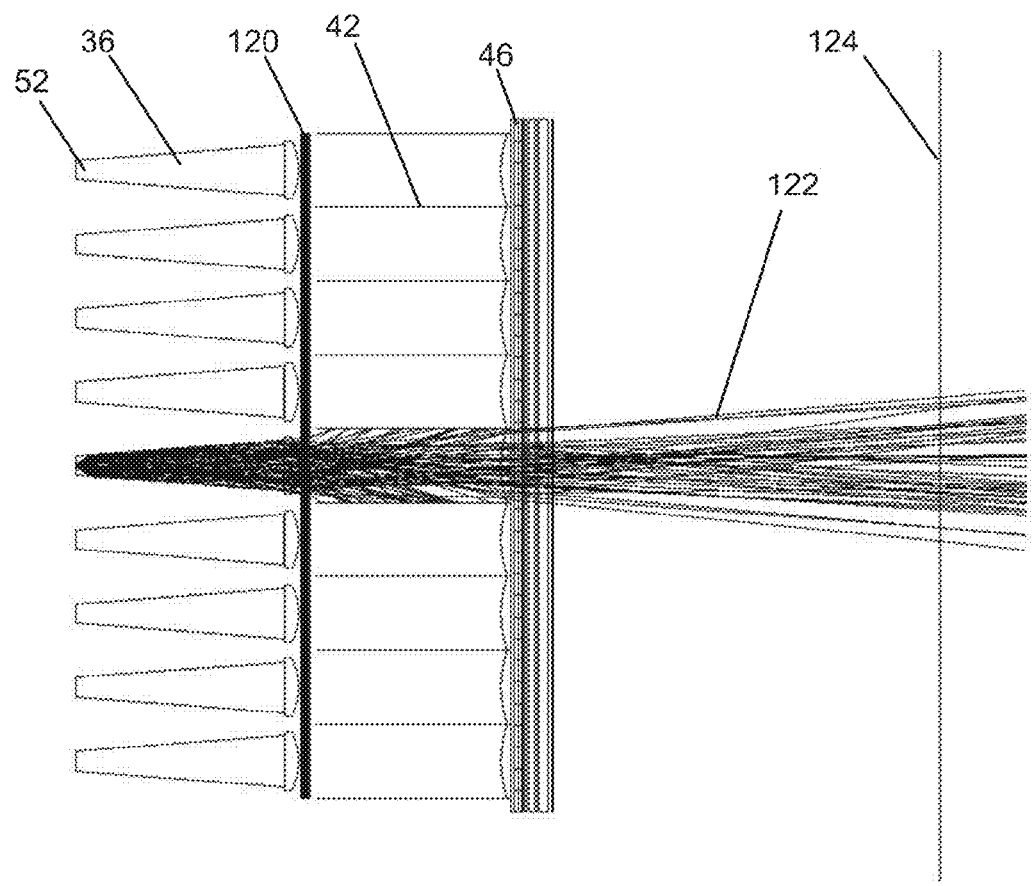
Figure 12:
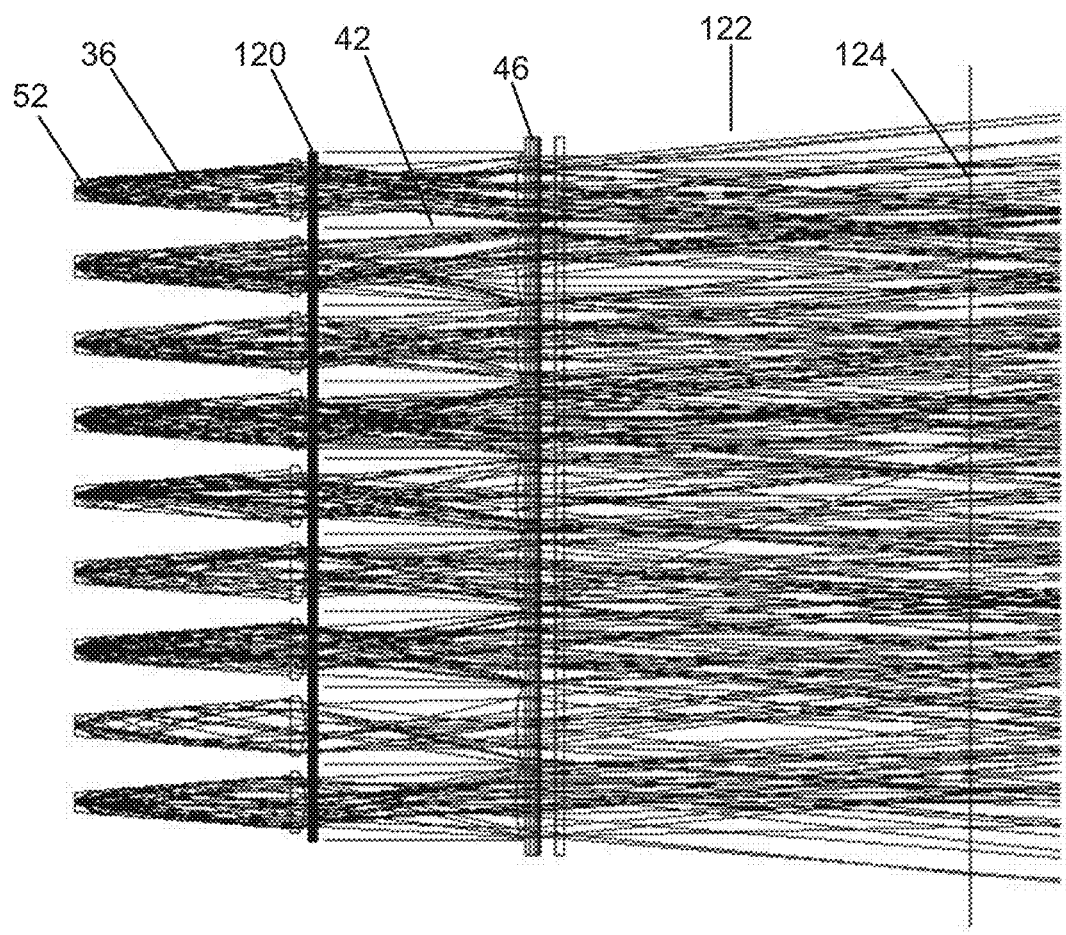
FIG. 12 is a diamgrammatic view of FIG. 11B with all 9 channels illuminated with rays traversing the space between the LED and the illumination plane.

Referring now to FIG. 11A, a diagrammatic non-sequential ZEMAX raytrace of the Y-Z plane of the line source 30 of FIG. 2 showing only the optical components and the illumination plane 124 is shown. The rays 122 essentially pass through the taper 36 and diffuser 120 as if they were windows and are primarily only affected by the power of the common front lens element 118 of lens 46. The intensity profile in the Y-Z plane at 124 is an image of the input aperture of taper 36. Again, since the taper's input aperture is fully filled along the Y-Axis, the near field intensity at 124 in the Y-Axis is very uniform. The uniformity of the far field is a function of the lens aperture in the Y-Axis at lens 46 being uniformly filled. FIG. 11B shows a diagrammatic top view of FIG. 11A, showing the spreading effect of the diffuser 120 in the X-Z plane, which results in rays diffusing to greater angles and therefore impinging upon and being absorbed by the baffles 42. The far field angle exiting a given taper is a function of the ratio between the input and output dimensions. For example, assuming a Lambertian angular distribution of the LED source, which emits into a hemisphere and accepted by the taper at its input aperture, the output angle would be reduced according to the conservation of Etendue, or the Brightness Theorem. That is, the product of the linear dimension of the aperture and the numerical aperture (NA), which is equivalent to the product of the index of refraction, in this case air at 1.0, and the sine of the half-angle, is conserved. For example, if the ratio of the input to output aperture linear dimension is 0.50, then the limiting half-angle leaving the taper with an output face normal to the optical axis, would be the inverse sine of 0.50, which is 30 degrees. It should be clear that the ratios of the input to output aperture dimensions are much different for the taper 36. Therefore, the angle exiting the taper in the X-Z plane would be expected to be much larger. This means that even without the diffuser, the light exiting the taper in the X-Z plane would impinge on the baffles. The near field intensity at the output of a taper is very uniform, however, the far field is not, so the purpose of placing the diffuser near the output of the taper is to act to redistribute the far field from each point in the output face of the taper such as to achieve substantially uniform light in the far field from the perspective of the light which reaches the illumination plane as imaged by lens 116 of composite lens 46. Another view of FIG. 11B is shown in FIG. 12 for which all channels are ray traced to show the composite beam impinging on illumination plane 124. The plot shows only those rays that reach the illumination plane. The rays that impinge on the light absorbing baffles are not shown. This trace is for the center of three LEDs in each aperture 52. The effect of the off-axis position of the two LEDs that would be on either side is to produce a very slight offset in the distribution at illumination plane 124 along the X-axis.

Figure 13:
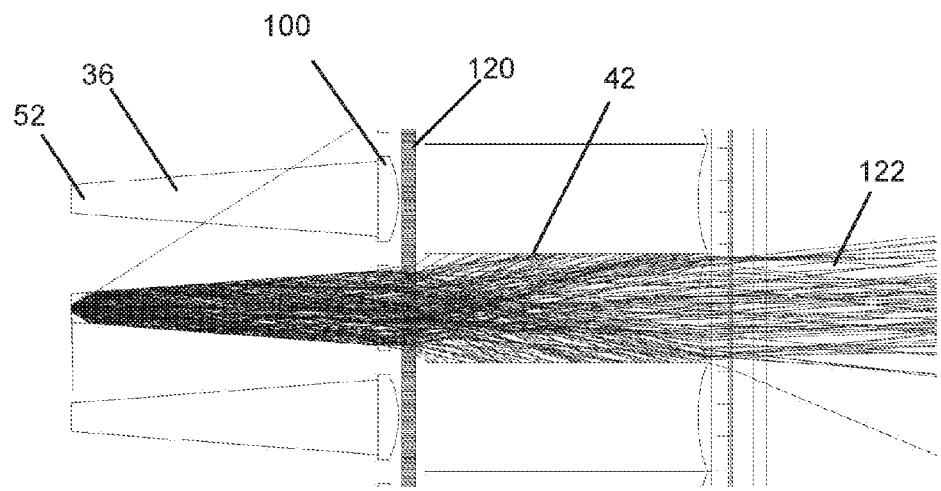
FIGS. 13A and 13B show diagrammatic views of closer detail of a single channel as depicted in FIG. 11B indicating all rays leaving a single LED on the central axis of the taper, including those absorbed by the baffles in FIG. 13A and only those reaching the illumination plane in FIG. 13B.
Figure 13:
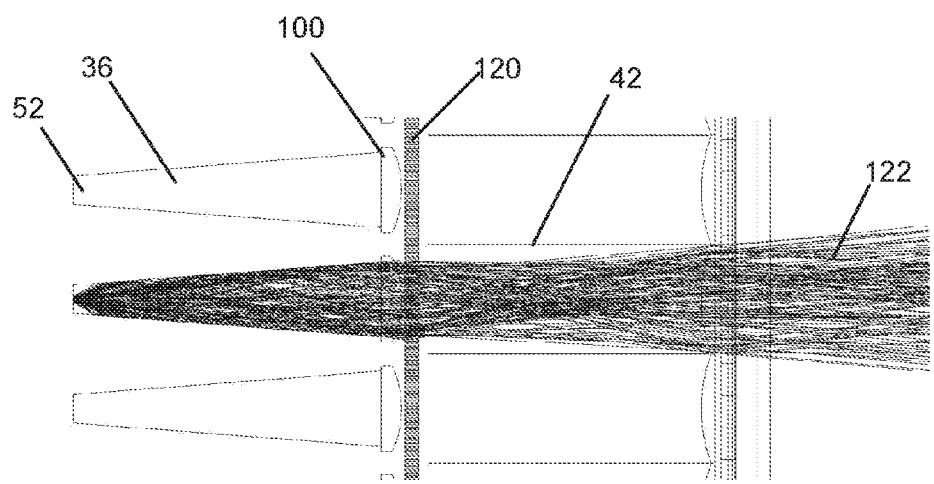
Figure 14:
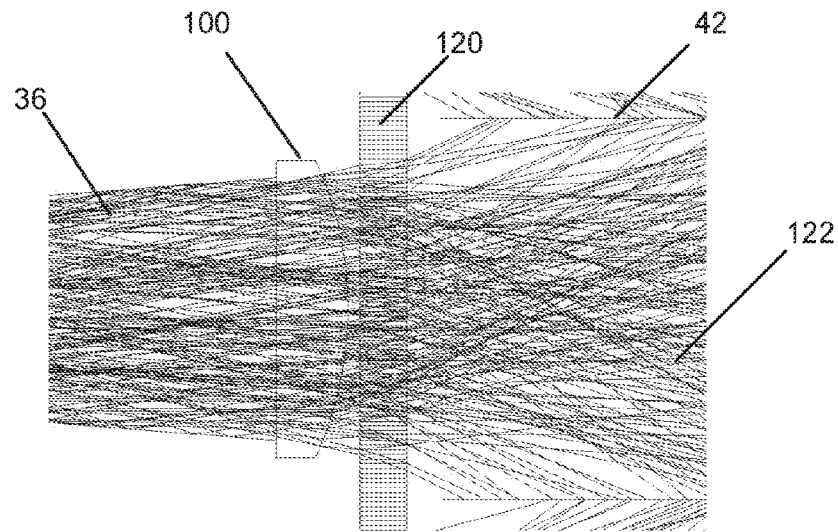
FIGS. 14A and 14B show diagrammatic close up views of the region in the vicinity of the diffuser at the exit of the taper's field lens as shown in FIGS. 13A and 13B, respectively.
Figure 14:
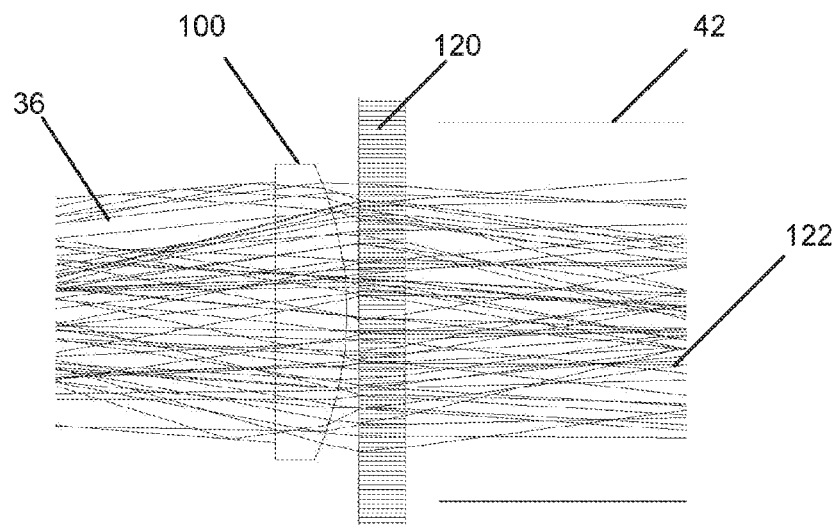

Referring now to FIGS. 13A and 13B, a close up diagrammatic top view of a single channel as shown in FIG. 11B is shown with all rays viewed and with only those rays that reach the illumination plane shown, respectively. FIGS. 14A and 14B show an even closer view of FIGS. 13A and 13B, respectively, of the region in the vicinity of the output of the taper field lens 100 and the diffuser 120 indicating how rays are deflected into different angles in the far field, thereby increasing far field uniformity. For example, note the bottom ray of ray set 122 passing through the diffuser 120 of FIG. 14B as it is deviated by lenticular cylindrical lens elements back toward the optical axis.

Figure 15:
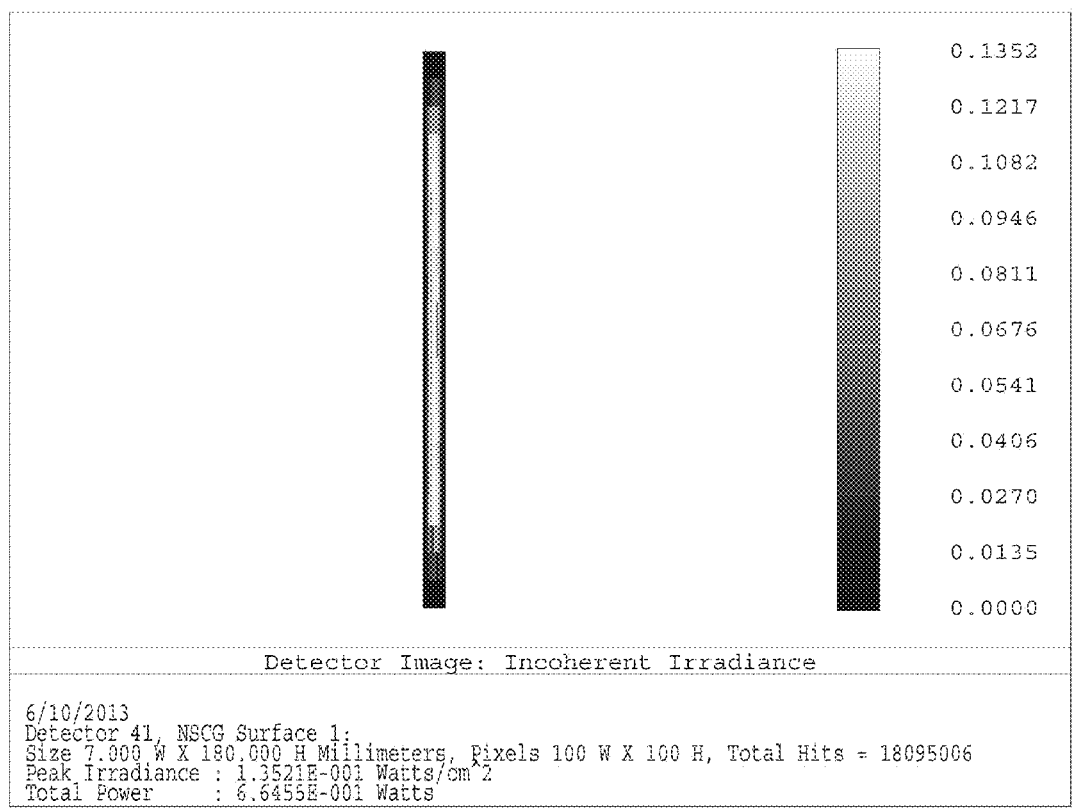
FIG. 15A through 15C show the near field intensity of the system of FIG. 1 in grayscale, Y-Axis, and X-Axis profiles, respectively.
Figure 15:
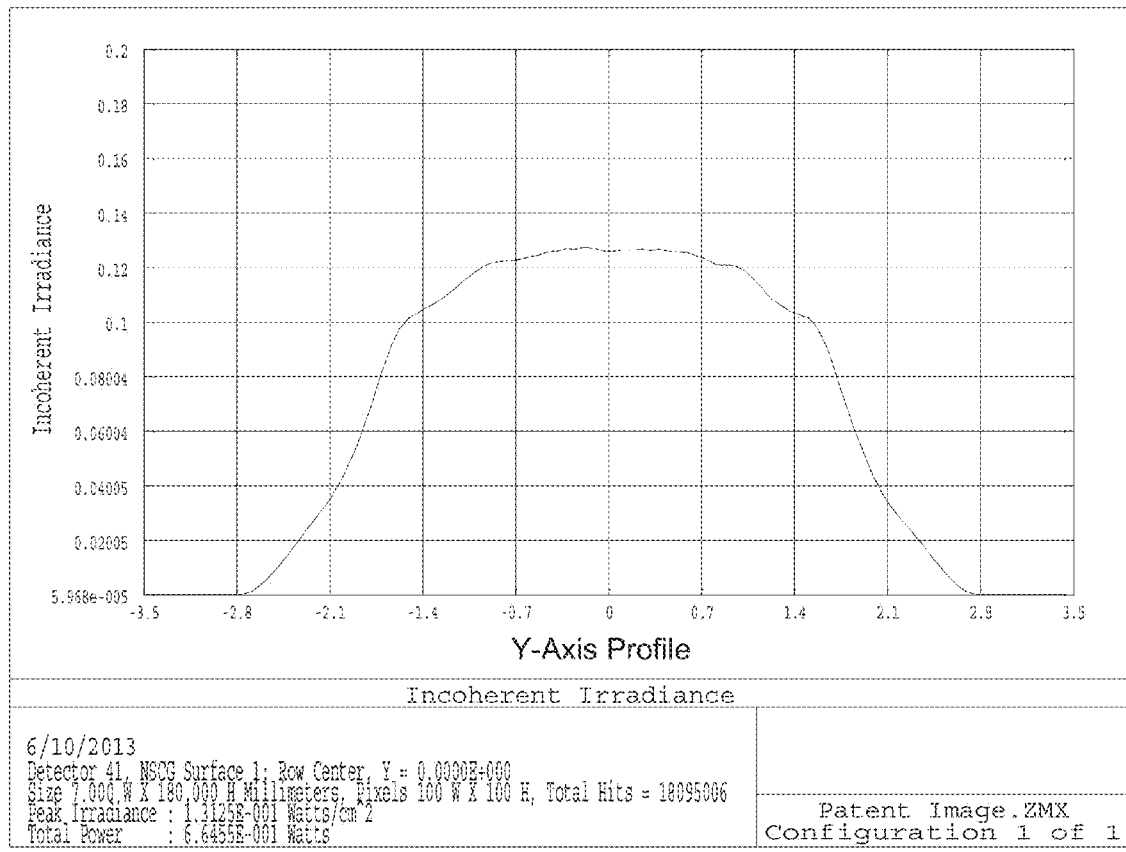
Figure 15:
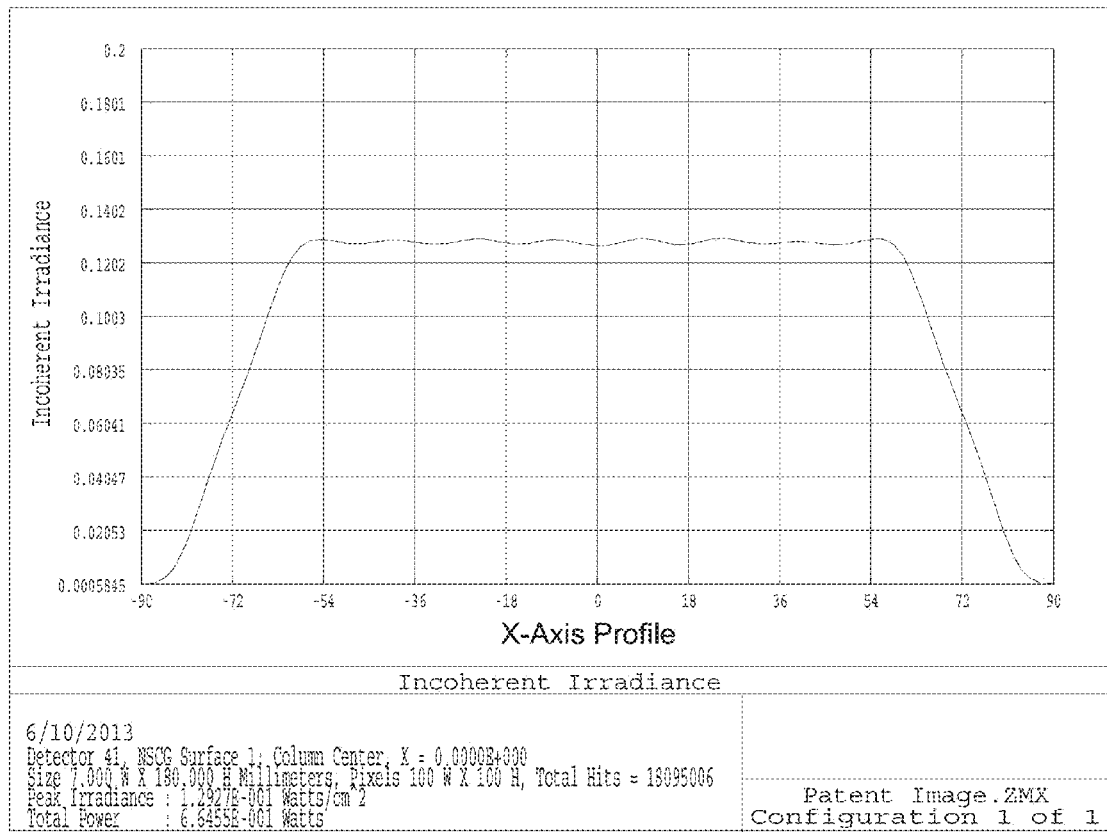

Referring now to FIG. 15A, shown is a grayscale plot of the near field intensity distribution at the illumination plane of the system 30 of FIG. 2. This line source intensity distribution is shown in the Y-Axis profile in FIG. 15B representing the narrow dimension of the line and in the X-Axis profile in FIG. 15C representing the long dimension of the line source near field intensity distribution. The small modulation ripples along the length of the line in FIG. 15C are a consequence of the superposition of each of the line sources in the illumination plane. That is, since the line source is a linear system, the total near field intensity distribution is the sum of the individual near field intensity distributions from each channel. In this case, only the nearest neighboring adjacent channels contribute to the intensity at any given point along the line. This near field intensity distribution would be changed by limiting the numerical aperture of the camera lens system. As the angular extent of the acceptance angle of a given camera lens decreases, that is the numerical aperture decreases, the peak to valley modulation depth will increase as well. This degree of ripple is affected by the center to center spacing of the LED channels and as described previously, is optimized by non-sequential modeling to a specific specification of focal length (working distance) and far field angle. The far field angle is generally chosen to somewhat overfill the numerical aperture of the greatest camera working numerical aperture, thereby maximizing signal to noise ratio (SNR). With reference to the profile of FIG. 15B, it is desirable to have the width of the line source substantially flat over the field of view of the camera along the narrow dimension of the line, plus some margin for alignment tolerance. The width of the line can easily be increased by increasing the height along the Y-Axis of the input aperture of the taper 36, but too large an increase can result in an increase of stray light. Additionally, increasing the input aperture in the Y-Axis does not increase the intensity, but only increases the width of the line.

Figure 16:
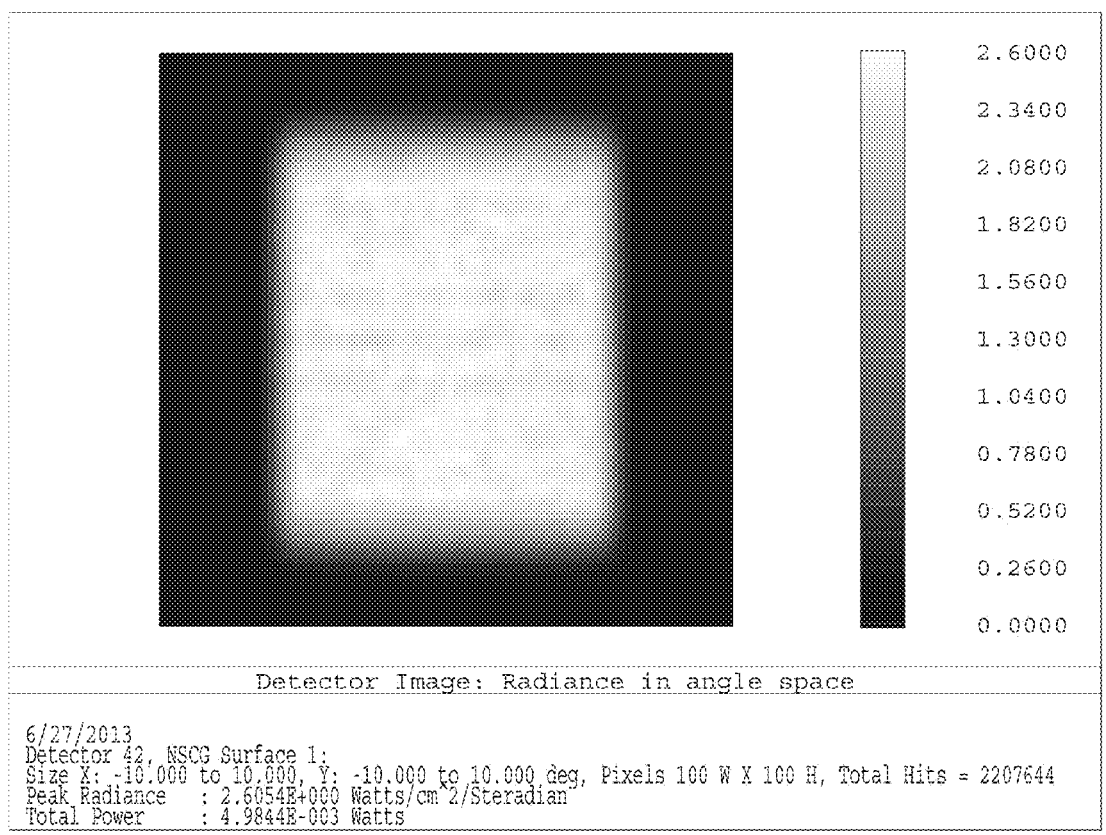
FIG. 16A through 16C show the far field intensity of the system of FIG. 1 in grayscale, Y-Axis, and X-Axis profiles, respectively.
Figure 16:
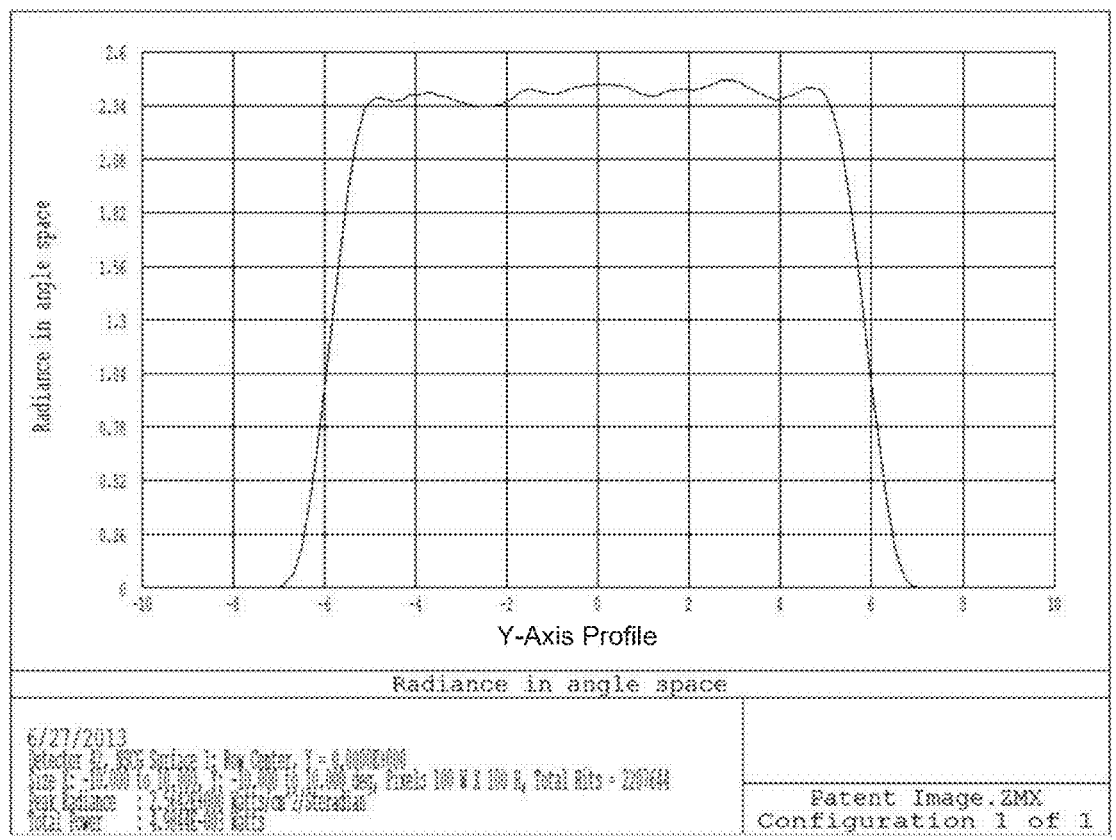
Figure 16:
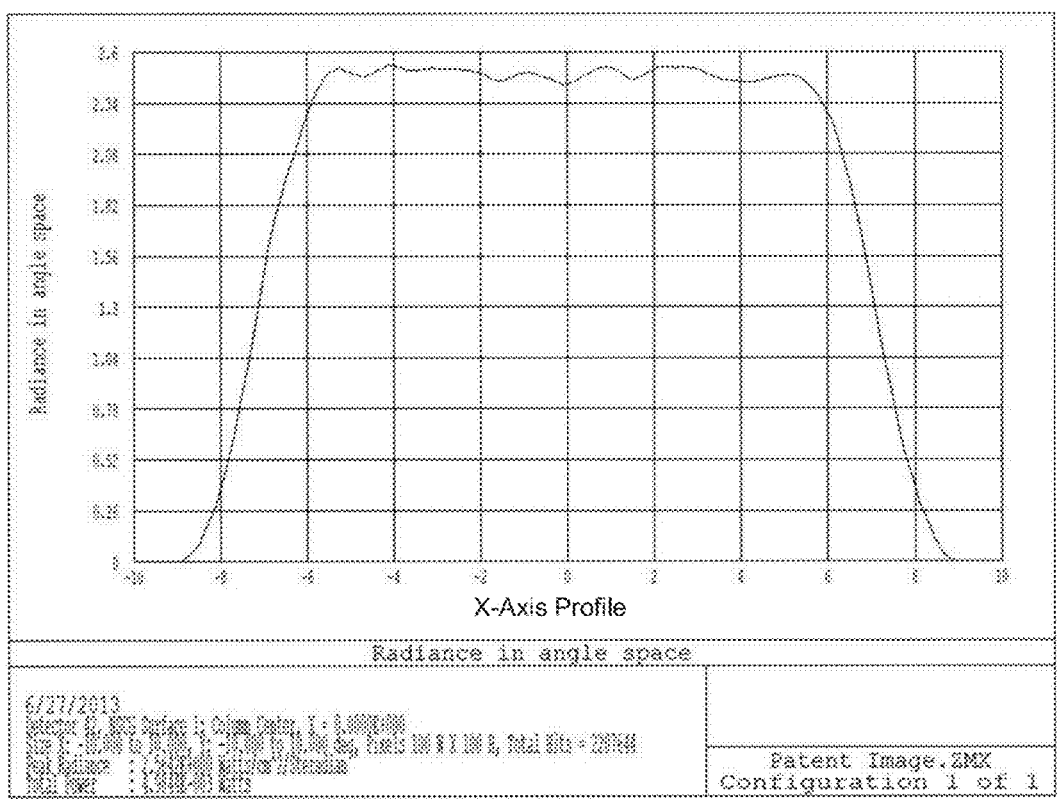

Referring now to FIG. 16A, a grayscale plot of the far field intensity distribution at the illumination plane of the system 30 of FIG. 2 is shown. This line source far field intensity distribution is shown in the Y-Axis profile in FIG. 16B and in the X-Axis profile in FIG. 15C.

Figure 17:
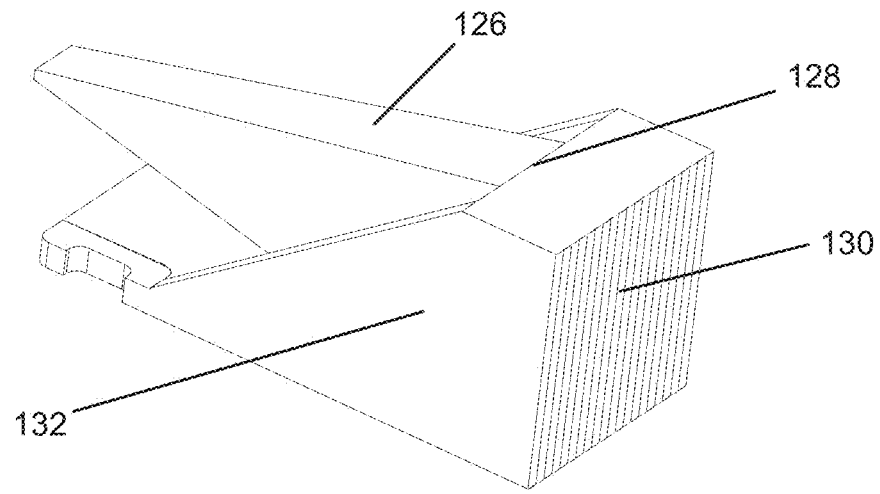
FIGS. 17A and 17B show diagrammatic alternative embodiments of the taper of FIG. 9 with the diffusing lenticular lens built directly onto the face of a flat and curved output face, respectively.
Figure 17:
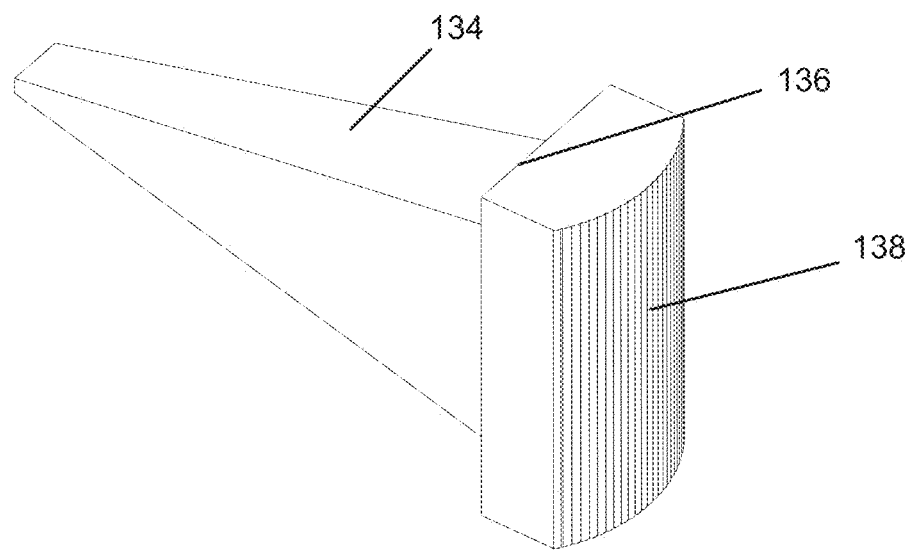

Referring now to FIG. 17A, a diagrammatic isometric view of an alternative embodiment of the taper 36 is shown with taper section 126, output aperture 128, integral diffusing lenticular 130 molded in, and holder section 132. The lenticular diffuser, or holographic diffuser, structure can be molded directly onto the output face of the taper to reduce cost and increase transmission by reducing additional Fresnel reflective losses resulting from the use of a separate diffusing element. An alternative embodiment to FIG. 17A is shown in FIG. 17B which incorporates an output face 138 that is both curved to act as a taper field lens and has lenticular array cylindrical elements molded in to act as the diffusing element.

While the invention has been shown and described with reference to specific embodiments, it should be understood by those skilled in the art that various changes in form and detail may be made therein without departing from the spirit and scope of the invention.

What is claimed is:

1. A light emitting diode (LED) linear illumination system, comprising:
    a linear array of LED groups, each one of the LED groups having at least one LED and having an optical axis that is normal to a surface of each of the LEDs;
    a linear array of collection optics each disposed along a respective one of the optical axes and having an input aperture to collect radiation emitted from a respective one of the LED groups and having an output aperture through which the collected radiation propagates;
    a linear array of cylindrical field lenses each disposed on one of the optical axes, the linear array of cylindrical field lenses having a first side adjacent to the output aperture of a respective one of the collection optics and a second side opposite to the first side;
    a diffuser disposed substantially adjacent to the second side of the linear array of cylindrical field lenses, the diffuser increasing a far field uniformity of the radiation emitted from the LED groups;
    a plurality of cylindrical lenses each having a first focal length in a first plane and being disposed on one of the optical axes at a first distance from the output aperture of a respective one of the collection optics by substantially the first focal length to thereby image light from the output aperture to infinite; and
    a cylindrical lens having a second focal length in a second plane that is orthogonal to the first plane, the cylindrical lens being disposed substantially at a second distance from the input apertures of the linear array of collection optics to form an image of the input apertures in the second plane at an image plane.

2. The LED linear illumination system of claim 1 wherein each one of the collection optics is a compound parabolic concentrator (CPC) having a rectangular input aperture and a rectangular output aperture.

3. The LED linear illumination system of claim 2 wherein each one of the CPCs has straight wall sections disposed between the input aperture and a CPC section in the form of a theta-by-theta concentrator.

4. The LED linear illumination system of claim 3 wherein each one of the CPCs has straight walls along a first pair of opposite sides and curved walls along a second pair of opposite sides.

5. The LED linear illumination system of claim 1 further comprising a plurality of baffles each comprising a surface comprising a light absorbing material arranged parallel to an adjacent pair of optical axes and extending from the linear array of cylindrical field lenses to the plurality of cylindrical lenses.

6. The LED linear illumination system of claim 1 wherein a portion of the diffuser is formed at the output aperture of each one of the collection optics.

7. The LED linear illumination system of claim 1 wherein a portion of the diffuser is formed on a surface of each one of the cylindrical field lenses.

8. The LED linear illumination system of claim 1 wherein each of the cylindrical field lenses is formed on a respective one of the collection optics at the exit aperture and is integral with the collection optic.

9. The LED linear illumination system of claim 1 wherein each one of the collection optics is a taper.

10. The LED linear illumination system of claim 1 further comprising a plurality of aperture stops each disposed on one of the optical axes substantially adjacent to a respective one of the field lenses.

11. The LED linear illumination system of claim 1 further comprising a plurality of aperture stops each disposed on one of the optical axes substantially adjacent to a surface of the diffuser that is opposite to the linear array of cylindrical field lenses.

12. A light emitting diode (LED) linear illumination system, comprising:
    a linear array of LED groups, each one of the LED groups having at least one LED and having an optical axis that is normal to a surface of each of the LEDs;
    a linear array of tapers each disposed along a respective one of the optical axes and having an input aperture to collect radiation emitted from a respective one of the LED groups and having an output aperture through which the collected radiation propagates;
    a linear array of cylindrical field lenses each disposed on one of the optical axes adjacent to the output aperture of a respective one of the tapers;
    a diffuser disposed adjacent to the linear array of cylindrical field lenses;
    a plurality of aperture stops each disposed on one of the optical axes substantially adjacent to a surface of the diffuser that is opposite to the linear array of cylindrical field lenses;
    a plurality of cylindrical lenses each having a first focal length in a first plane and being disposed on one of the optical axes at a first distance from the output aperture of a respective one of the tapers by substantially the first focal length to thereby image light from the output aperture to infinite;
    a cylindrical lens having a second focal length in a second plane that is orthogonal to the first plane, the cylindrical lens being disposed substantially at a second distance from the input apertures of the linear array of tapers to form an image of the input apertures in the second plane at an image plane; and
    a plurality of baffles each comprising a surface comprising a light absorbing material arranged parallel to an adjacent pair of optical axes and extending from the linear array of cylindrical field lenses to the plurality of cylindrical lenses.

13. The LED linear illumination system of claim 12 wherein the diffuser comprises a plurality of diffusers disposed adjacent to the linear array of cylindrical field lenses.

* * * * *